(12) United States Patent
Lee et al.

(10) Patent No.: US 11,103,599 B2
(45) Date of Patent: Aug. 31, 2021

(54) NANOCARRIERS FOR PROSTATE CANCER CELL TARGETED THERAPY AND/OR DIAGNOSIS THEREOF

(71) Applicant: CHANGWON NATIONAL UNIVERSITY INDUSTRY UNIVERSITY COOPERATION FOUNDATION, Changwon-si (KR)

(72) Inventors: Yong Ill Lee, Changwon-si (KR); Sharipov Mirkomil, Changwon-si (KR)

(73) Assignee: Changwon National University Industry University Cooperation Foundation, Changwon-si (KR)

( * ) Notice: Subject to any disclaimer, the term of this patent is extended or adjusted under 35 U.S.C. 154(b) by 76 days.

(21) Appl. No.: 16/467,770

(22) PCT Filed: Apr. 11, 2018

(86) PCT No.: PCT/KR2018/004254
§ 371 (c)(1),
(2) Date: Jun. 7, 2019

(87) PCT Pub. No.: WO2018/190639
PCT Pub. Date: Oct. 18, 2018

(65) Prior Publication Data
US 2019/0321491 A1    Oct. 24, 2019

(30) Foreign Application Priority Data

Apr. 14, 2017 (KR) .................. 10-2017-0048783

(51) Int. Cl.
| | |
|---|---|
| *A61K 49/18* | (2006.01) |
| *A61K 49/00* | (2006.01) |
| *A61K 9/107* | (2006.01) |
| *A61K 31/565* | (2006.01) |
| *A61K 47/24* | (2006.01) |

(52) U.S. Cl.
CPC ........ *A61K 49/0065* (2013.01); *A61K 9/1075* (2013.01); *A61K 31/565* (2013.01); *A61K 47/24* (2013.01); *A61K 49/0019* (2013.01); *A61K 49/0082* (2013.01)

(58) Field of Classification Search
CPC .......... A61K 9/50; A61K 9/51; A61K 9/5107; A61K 9/513; A61K 9/5146; A61K 9/5169; A61K 9/5192; A61K 49/18; A61K 49/1818; A61K 49/1809; A61K 49/1812
See application file for complete search history.

(56) References Cited

U.S. PATENT DOCUMENTS 4,770,183 A    9/1988 Groman et al.

FOREIGN PATENT DOCUMENTS

WO    WO-2015140160 A1 *    9/2015    ......... A61K 31/7008

OTHER PUBLICATIONS

Chen et al (Phospholipid-modified Upconversion Nanoprobe for Ratiometric Fluorescence Detection and Imaging of Phospholipase D in Cell Lysate and in Living Cells, Analytical Chemistry, 2015, 86, 7119-7127) (Year: 2015).*
Matthew V. Dacosta, et al., "Analytica Chimica Acta," 832 (2014) pp. 1-33.
Chao Wang et al., "Biomaterials," 32 (2011) pp. 6145-6154.
Anna Gnach et al., "Chem Soc Rev," (2015), 44, pp. 1561-1584.
Simona Mura et al., "Nature Materials," (2013), 12, pp. 991-1003.
Kyung Hyun Min et al., "Journal of Controlled Release," 114 (2010) pp. 259-266.
Cen, Yao et al, "Phospholipid-modified upconversion nanoprobe for ratiometric fluorescence detection and imaging of phospholipase d in cell lysate and in living cells," Analytical Chemistry,(2014), 86, pp. 7119-7127.
Sved, Paul et al,"Oncogenic action of secreted phospholipase A2 in prostate cancer," Cancer Research, 64, pp. 6934-6940, Oct. 1, 2004.
Yu, Yongjiang et al, "In-vitro and in-vivo imaging of prostate tumor using NaYF4: Yb, Er up-converting nanoparticles," Pathology & Oncology Research, 2014, 20, pp. 335-341.
Yuan, Yingying et al, "A facile supramolecular approach to fabricate multifunctional upconversion nanoparticles as a versatile platform for drug loading, in vivo delivery and tumor imaging," Journal of Materials Chemistry B, 2017, 5, pp. 2425-2435.
Sharipov, Mirkomil et al, "Phospholipase A2-responsive phosphate micelleloaded UCNPs for bioimaging of prostate cancer cells," Scientific Reports, 2017, 5, pp. 2425-2435.

(Continued)

*Primary Examiner* — Micah Paul Young
(74) *Attorney, Agent, or Firm* — Harness, Dickey & Pierce, P.L.C.

(57) ABSTRACT

The present invention relates to a nanocarrier for targeted therapy and/or diagnosis of a prostate cancer cell, the nanocarrier including a micelle including a phosphate surfactant represented by a specific Chemical Formula. The micelle including the phosphate surfactant constituting the nanocarrier for targeted therapy and/or diagnosis of the prostate cancer cell according to the present invention is cleaved by the overexpressed enzyme in the vicinity of the prostate cancer cell, so that therapeutic agent or diagnostic agent particles loaded on the micelle are capable of being selectively released to the prostate cancer cell. Therefore, it is possible to maximize the therapeutic and/or diagnostic effects while remarkably reducing the side effects of the drug in the living body compared to a conventional technology.

12 Claims, 32 Drawing Sheets

(56) References Cited

OTHER PUBLICATIONS

International Search Report PCT/ISA/210 for International Application No. PCT/KR2018/004254 dated Jul. 24, 2018.
Graff, Jeremy R., et al., "Expression of Group IIa Secretory Phospholipase A2 Increases wiht Prostate Tumor Grade", Advances in Brief, Clinical Cancer Research, vol. 7, pp. 3857-3861, Dec. 2001.

* cited by examiner

NANOCARRIERS FOR PROSTATE CANCER CELL TARGETED THERAPY AND/OR DIAGNOSIS THEREOF

CROSS-REFERENCE TO RELATED APPLICATIONS

This application is a national phase under 35 U.S.C. § 371 of PCT International Application No. PCT/KR2018/004254 which has an International filing date of Apr. 11, 2018, which claims priority to Korean Application No. 10-2017-0048783, filed Apr. 14, 2017, the entire contents of each of which are hereby incorporated by reference.

TECHNICAL FIELD

The present invention relates to a nanocarrier which carries a therapeutic agent and/or a diagnostic agent of prostate cancer and which has high selectivity to a prostate cancer cell.

BACKGROUND ART

Research is being actively performed to develop a technology for improving drug efficacy and reducing side effects by effectively accumulating a large amount of drugs in desired targets such as in-vivo organs, tissues, cells, or cell organelles while reducing undesired accumulation thereof in nontarget tissues.

Meanwhile, the diagnosis of cancer cells, particularly the diagnosis of cancer cells in the early stages, has attracted great interest from researchers, with the incidence of more than 14 million cancer cases worldwide every year. One of the well-known contrast medium nanoparticles used to diagnose liver-tissue-related diseases is Feridex, which is a superconductive iron oxide nanoparticle coated with dextran.

However, toxicity and low dispersibility are still considered a problem upon the application of drug or imaging agent nanoparticles to biological systems as described above. Accordingly, nanoparticle surface modification, which includes the use of biocompatible chemical materials and biologic entities such as aptamers, antibodies, sugars, and folic acid, has been proposed as a solution in order to reduce cytotoxicity to non-cancerous cells by increasing selectivity to specific tumor cells and also improving dispersibility.

However, in consideration of the complexity of the method of distributing a drug or imaging-agent nanoparticles to the target, metabolism, and release, the design of a complete delivery system is a complex task that is still difficult to solve.

DISCLOSURE

Technical Problem

An object of the present invention is to provide a novel nanocarrier for targeted therapy and/or diagnosis of prostate cancer cells. The nanocarrier is capable of minimizing side effects and also maximizing therapeutic and/or diagnostic effects due to a reduction in the dosage of the drug and/or diagnostic agent particles by selectively releasing therapeutic agent and/or diagnostic agent particles at specific positions in the living body, specifically in the vicinity of the prostate cancer cell.

Technical Solution

In order to accomplish the above object, the present invention provides a nanocarrier for targeted therapy and/or diagnosis of a prostate cancer cell. The nanocarrier includes a micelle including a phosphate surfactant represented by the following Chemical Formula.

[Chemical Formula]

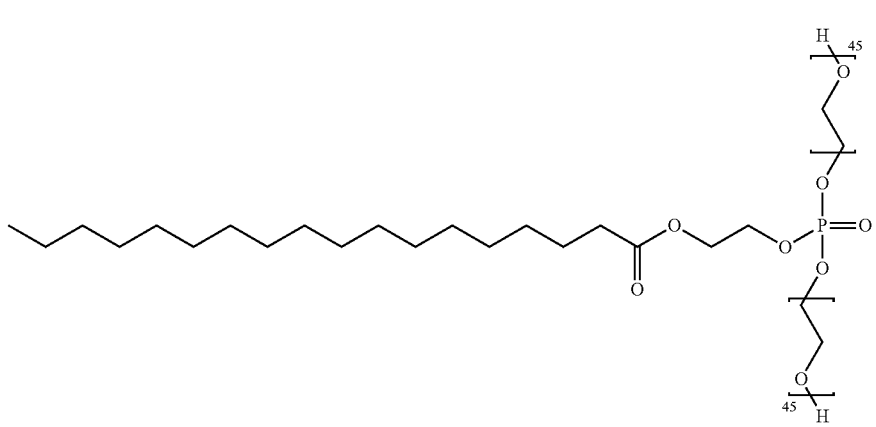

Further, therapeutic agent and/or diagnostic agent particles that are carried in the nanocarrier for targeted therapy and/or diagnosis of the prostate cancer cell are selectively released to the prostate cancer cell.

Further, in the nanocarrier for targeted therapy and/or diagnosis of the prostate cancer cell, an ester group contained in a phosphate surfactant is hydrolyzed by a secretory phospholipase A2 (sPLA-2) overexpressed in the prostate cancer cell, thus releasing the therapeutic agent and/or diagnostic agent particles.

In addition, in another aspect of the invention, the present invention provides bio-imaging particles including the nanocarrier and a diagnostic agent loaded on the nanocarrier.

Further, the diagnostic agent is a fluorescent agent, a radioactive agent, or a contrast medium.

Further, the diagnostic agent is upconversion fluorescent nanoparticles.

Further, the upconversion fluorescent nanoparticles include NaAF$_4$:B$_1$/B$_2$/B$_3$ (A is a lanthanide element and B$_1$, B$_2$, and B$_3$ are different rare earth elements).

Further, A is one selected from the group consisting of Y, Tb, Dy, Ho, Tm, Lu, La, Ce, Pr, Nd, Pm, Sm, and Eu.

Further, B$_1$, B$_2$, and B$_3$ are different from each other and are each one selected from the group consisting of Yb, Er, Sc, Y, La, Ce, Pr, Nd, Pm, Sm, Eu, Gd, Tb, Dy, Ho, Tm, and Lu.

In addition, in another aspect of the invention, the present invention provides a diagnosis method of prostate cancer. The diagnosis method includes disposing the above-described bio-imaging particles in a biological environment and selectively releasing diagnostic agent particles onto the surface of a prostate cancer cell positioned in the biological environment, thus performing delivery.

In addition, in another aspect of the invention, the present invention provides a drug delivery substance including the nanocarrier and a prostate cancer therapeutic agent loaded on the nanocarrier.

In addition, in another aspect of the invention, the present invention provides a prostate cancer therapy method. The therapy method includes disposing the above-described drug delivery substance in a biological environment and selectively releasing therapeutic agent particles onto the surface of a prostate cancer cell positioned in the biological environment, thus performing delivery.

In addition, in another aspect of the invention, the present invention provides a pharmaceutical composition for prostate cancer therapy including the above-described drug delivery substance as an active ingredient.

Further, the pharmaceutical composition for prostate cancer therapy is in the form of an injection, a liquid medicine, a powder remedy, a suspension, a granule, a syrup, a capsule, a pill, or a tablet.

Advantageous Effects

In a micelle including a phosphate surfactant constituting a nanocarrier for targeted therapy and/or diagnosis of a prostate cancer cell according to the present invention, since chemical bonds are cleaved by the overexpressed enzyme in the vicinity of the prostate cancer cell, therapeutic agent or diagnostic agent particles loaded on the micelle are capable of being selectively released only to the prostate cancer cell. Therefore, it is possible to maximize therapeutic and/or diagnostic effects while remarkably reducing the side effects of drugs in the living body compared to a conventional technology.

BEST MODE

Hereinafter, the present invention will be described in detail.

A nanocarrier for targeted therapy and/or diagnosis of a prostate cancer cell according to the present invention includes a micelle including a phosphate surfactant represented by the following Chemical Formula.

Figure 1:
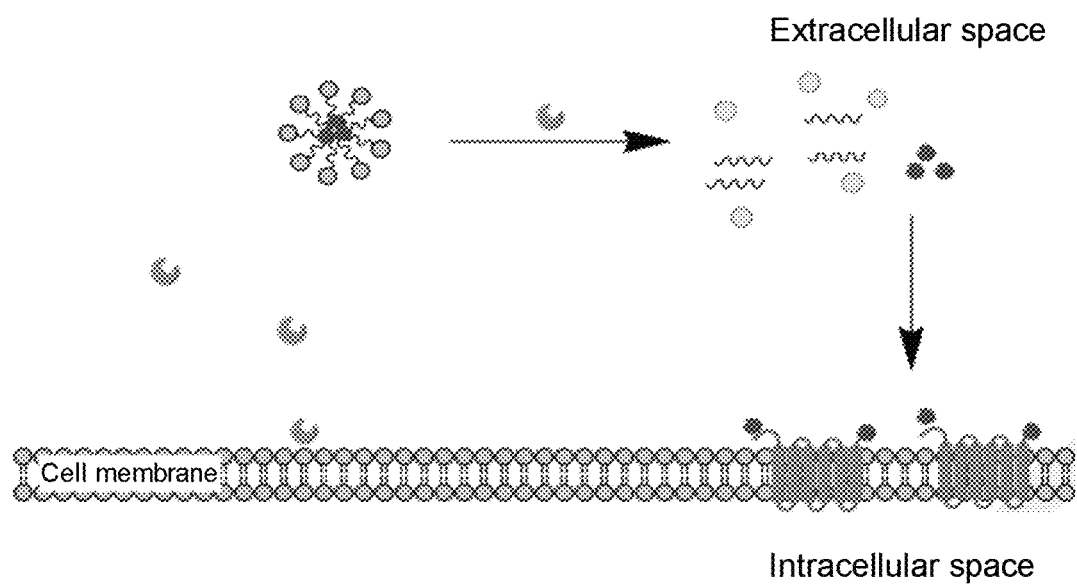
FIG. 1 is a schematic view showing an example of a mechanism in which upconversion fluorescent nanoparticles contained in bio-imaging particles according to the present invention are selectively delivered to a prostate cancer cell.
Figure 2:
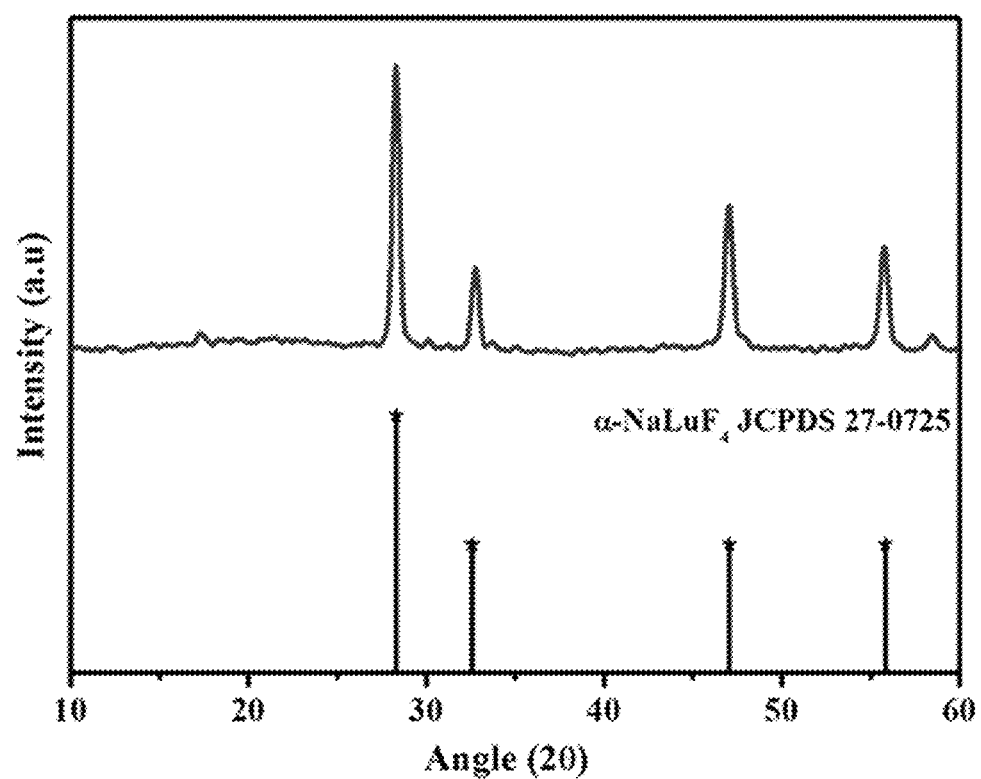
FIG. 2 is an XRD pattern of NaLuF$_4$:Gd$^{3+}$/YB$^{3+}$/Er$^{3+}$ upconversion nanoparticles functionalized with carboxyl.
Figure 3:
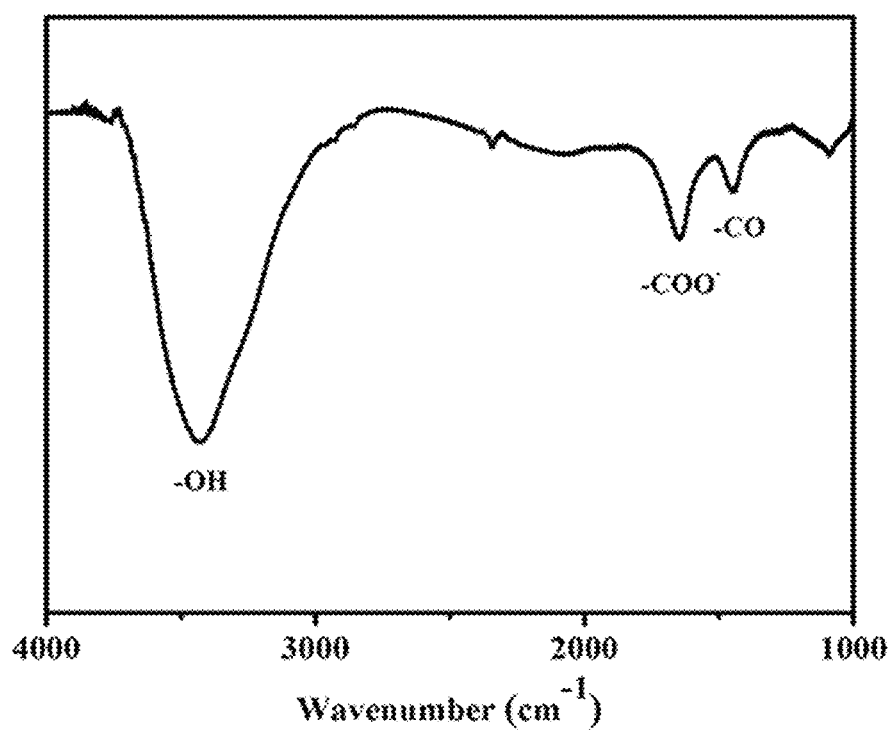
FIG. 3 is an FT-IR spectrum of NaLuF$_4$:Gd$^{3+}$/YB$^{3+}$/Er$^{3+}$ upconversion nanoparticles functionalized with carboxyl.
Figure 4:
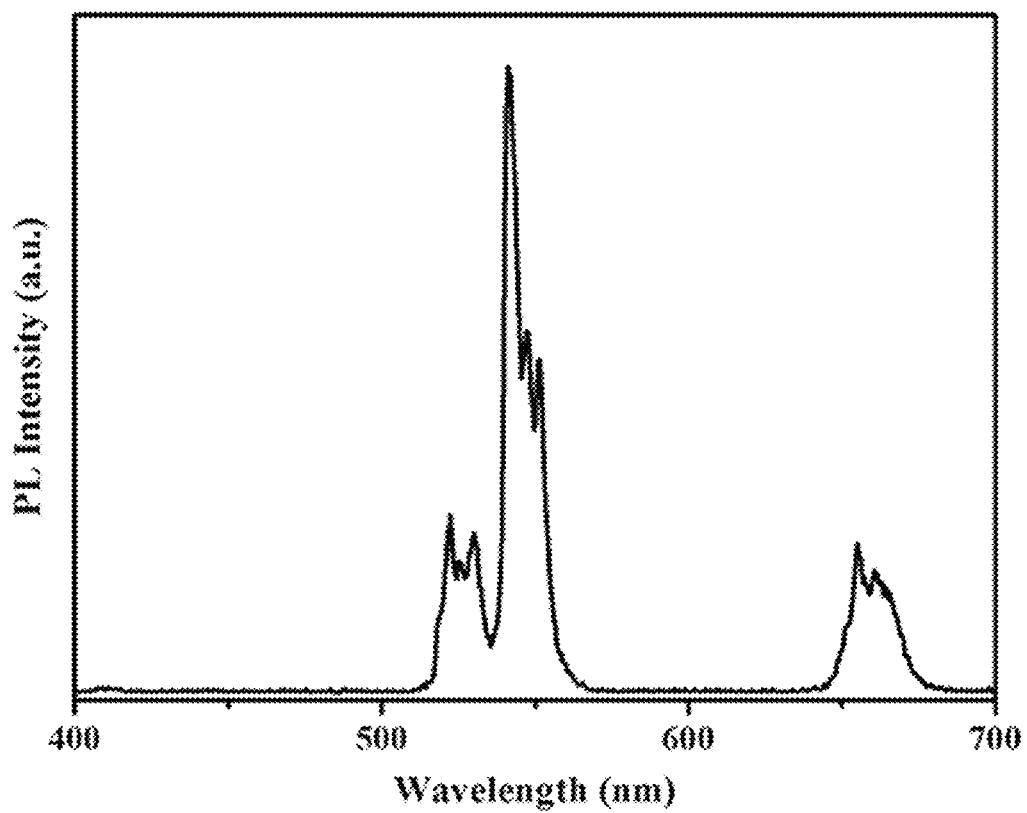
FIG. 4 is a photoluminescence spectrum of NaLuF$_4$:Gd$^{3+}$/YB$^{3+}$/Er$^{3+}$ upconversion nanoparticles functionalized with carboxyl.
Figure 5:
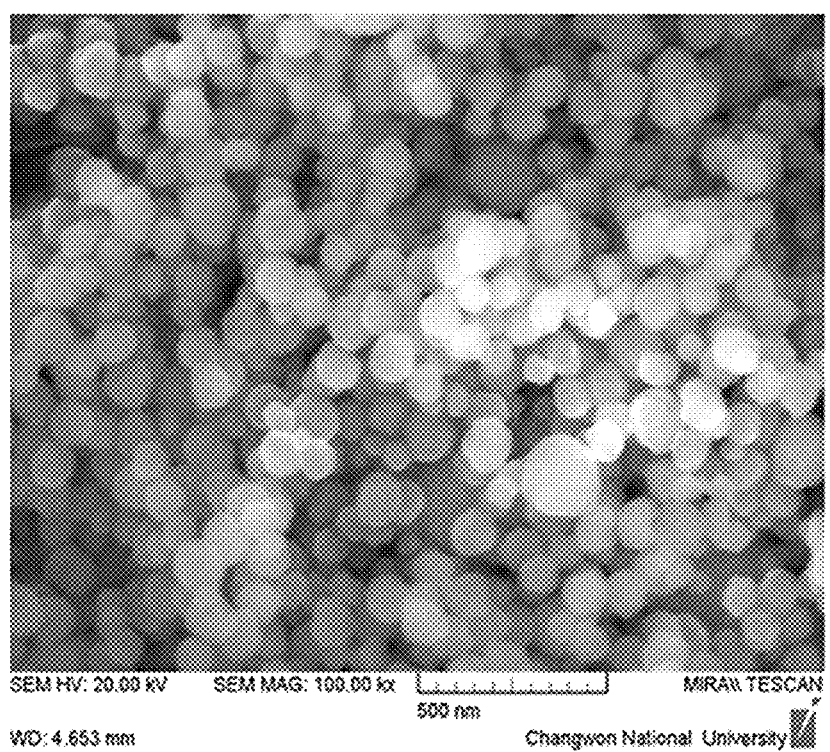
FIG. 5 shows a scanning electron microscope (SEM) image of NaLuF$_4$:Gd$^{3+}$/YB$^{3+}$/Er$^{3+}$ upconversion nanoparticles functionalized with carboxyl.

For example, referring to FIG. 1, showing an example of a mechanism in which the upconversion fluorescent nanoparticles contained in the bio-imaging particles according to the present invention are selectively delivered to prostate cancer cells, the ester group contained in the phosphate surfactant may be hydrolyzed by the secretory phospholipase A2 (sPLA-2) existing in a large amount in the vicinity of prostate cancer cells, so that the upconversion nanoparticles are selectively released from the carrier, thus effectively diagnosing prostate cancer using imaging of the prostate cancer cells.

Meanwhile, the upconversion fluorescent nanoparticles may include $NaAF_4:B_1/B_2/B_3$ (A is a lanthanide element and $B_1$, $B_2$, and $B_3$ are different rare earth elements), without limitation thereto.

[Chemical Formula]

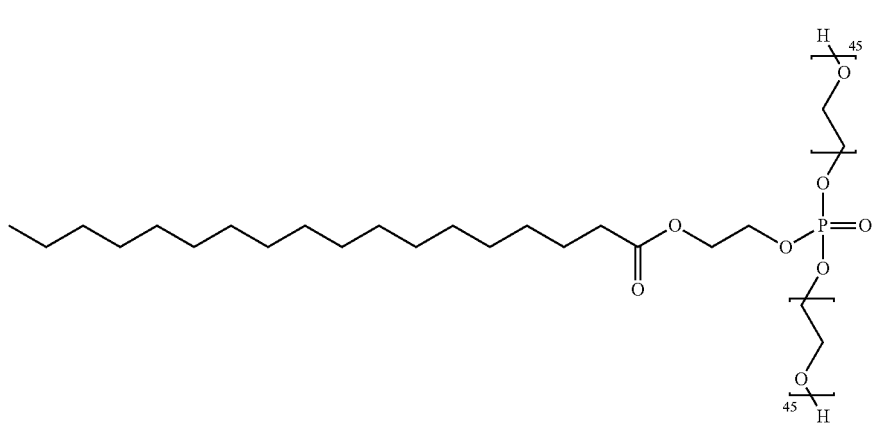

The phosphate surfactant is formed by phosphorylation of fatty acid ester and then PEGylation. The phosphate surfactant is synthesized from a bioaffinity amphipathic compound such as stearic acid (SA) and ethylene glycol (EG), thereby having biocompatibility.

Particularly, the phosphate surfactant is disintegrated in terms of the structure thereof by enzymes existing in the vicinity of the target in the living body, thereby serving to selectively release therapeutic agent and/or diagnostic agent particles loaded in the micelle or entrapped thereby onto the surface of the target prostate cancer cell.

More specifically, the ester group contained in the phosphate surfactant may be hydrolyzed by secretory phospholipase A2 (sPLA-2), which is overexpressed in the vicinity of prostate cancer cells and is present in a large amount, so that the therapeutic agent and/or diagnostic agent particles for prostate cancer, which are loaded or entrapped, are selectively released from the carrier, thereby exhibiting a marking effect for therapy and/or diagnosis through the death of prostate cancer cells.

For reference, the secretory phospholipase A2 (sPLA-2) is an enzyme that catalyzes the hydrolysis of phospholipid at the sn-2 position to thus generate fatty acid and lysophospholipid, and the overexpression thereof contributes to the proliferation of prostate cancer cells.

The nanocarrier according to the present invention may carry a diagnostic agent therein, thus forming bio-imaging particles for the diagnosis of prostate cancer.

As the diagnostic agent, a fluorescent agent, a radioactive agent, or a contrast medium may be used. More preferably, fluorescent nanoparticles having an upconversion luminescent property may be used.

A may be one selected from the group consisting of Y, Tb, Dy, Ho, Tm, Lu, La, Ce, Pr, Nd, Pm, Sm, and Eu. Further, $B_1$, $B_2$, and $B_3$ may be different from each other and may be each one selected from the group consisting of Yb, Er, Sc, Y, La, Ce, Pr, Nd, Pm, Sm, Eu, Gd, Tb, Dy, Ho, Tm, and Lu.

MODE FOR INVENTION

Hereinafter, the present invention will be described in detail with reference to Examples.

However, the following Examples may be modified into various other forms, and the scope of the present specification is not to be construed as being limited to the Examples described below. The Examples of the present specification are provided to more fully describe the present specification to those of ordinary skill in the art.

<Example 1> Manufacture of Phosphate Micelle Particles Loaded with UCNP (1) Synthesis of UCNP First, high-quality $NaLuF_4:Gd^{3+}/YB^{3+}/Er^{3+}$ upconversion nanoparticles that were functionalized with carboxyl were prepared using an easy single-step hydrothermal synthesis method using an aqueous solution. A stoichiometric amount of $NH_4F$ was added to a thoroughly agitated deionized-water solution containing NaCl, malonic acid (MA), and a $RECl_3$ solution, which was prepared in advance. Next, the solution was transferred to a Teflon-lined autoclave and heated to 200° C. for 8, 12, and 24 hours, and the obtained nanoparticles were collected by centrifugation, washed several times with ethanol and deionized water, and dried at 50°

C. for 24 hours. As a result of analysis of the properties thereof, it was found that the upconversion nanoparticles obtained through a hydrothermal reaction for 12 hours were more suitable.

Properties of the high-quality $NaLuF_4:Gd^{3+}/YB^{3+}/Er^{3+}$ upconversion nanoparticles that were functionalized with carboxyl were analyzed using XRD, FT-IR, photoluminescence, and Fe-SEM.

As shown in FIGS. 2 to 5, the peak of the XRD pattern of the $NaLuF_4:Gd^{3+}/YB^{3+}/Er^{3+}$ UCNP was indexed as a reference cubic $NaLuF_4$ pattern (JCPDS-27-0725), and no other impurity peak was detected. The carboxyl-functionalized surface of the $NaLuF_4:Gd^{3+}/YB^{3+}/Er^{3+}$ nanoparticles was confirmed by a FT-IR spectrum. The broad absorption band around 3435 $cm^{-1}$ corresponds to O—H stretching vibration. The sharp peak centered at 1632 $cm^{-1}$ is due to the carboxyl groups present on the surface of the nanoparticles. The band at 1434 $cm^{-1}$ is associated with the asymmetric stretching vibration of the carboxyl group (—COO—) chelated with the lanthanide ion causing the red shift of the carboxyl group. The single —CO stretching band of malonic acid is positioned at 1125 $cm^{-1}$. Photoluminescence shows the upconversion of near infrared rays to green and red light emission. The green emission at 540 nm is relatively stronger than the red emission. Fe-SEM photographs confirm the cubic shape of the UCNP, and show that the size of UCNP is in the range of 50 nm to 80 nm.

(2) Synthesis of Phosphate Polymer

Figure 6:
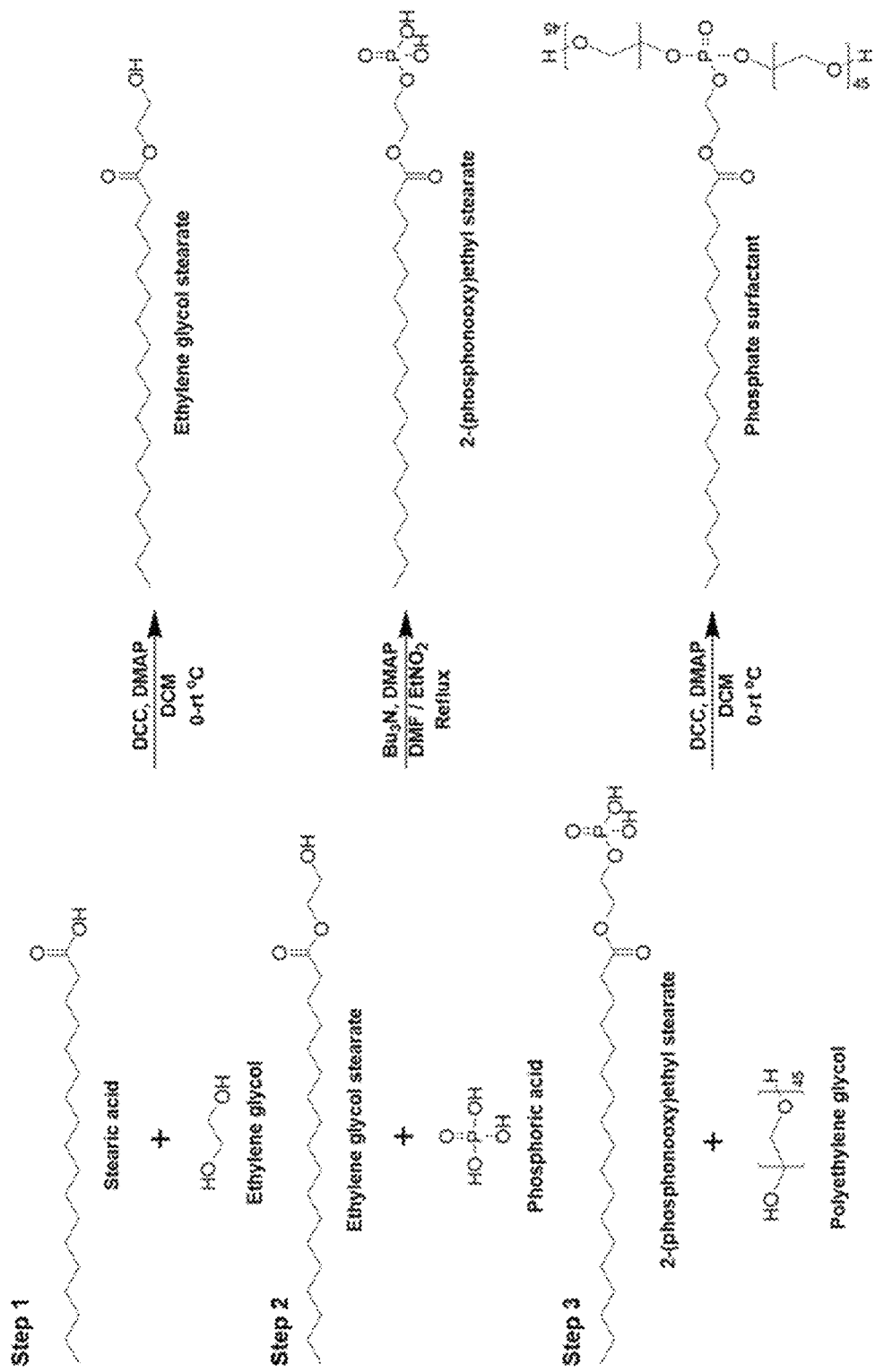
FIG. 6 is a view showing a three-step synthesis process of a phosphate surfactant.

As shown in FIG. 6, the phosphate surfactant was synthesized using a three-step synthesis process, and each step will be described in detail below.

1) First Step: Synthesis and Purification of Ethylene Glycol Stearate

Ethylene glycol stearate was synthesized using the Steglich esterification of carboxylic acid. This method is considered to be a green synthesis route because of the low reaction temperature thereof (0 to room temperature (RT)). After 0.005 mole (1.422 g) of stearic acid (SA) was dissolved in 30 ml of dichloromethane (DCM), 3 equivalents (0.9310 g) of ethylene glycol (EG) was added thereto, and agitation was performed in an ice-water bath, thus cooling a reaction medium. 4-dimethylaminopyridine (DMAP) was used as a catalyst in order to promote the reaction. The reaction medium was cooled to 0° C., and a solution which contained 2.27 g of dicyclohexylcarbodiimide (DCC) in 20 ml of DCM and which was prepared in advance was added dropwise thereto. After all of the DCC was added, the ice-water bath was removed and the reaction medium was agitated at room temperature for two days. When the reaction stopped, it was observed that a solid corresponding to dicyclohexylurea (DCU) was formed. In order to purify the reaction medium, filtration was performed, followed by washing three times with a saturated solution of sodium carbonate. After each washing, the product was filtered in order to remove the generated solids and simplify the separation of organic and aqueous phases. The product was then washed twice with the diluted hydrochloric acid solution. Recrystallization of the product was performed in the ice-water bath. The obtained product had traces of DCU that were capable of being dissolved in DCM. The solubility of DCU to methanol was very high, while ester was not dissolved in methanol, so the recrystallized product was washed with methanol for 5 minutes.

The molecular structure of the synthesized ethylene glycol stearate was confirmed using Fourier transform infrared spectroscopy (FT-IR) and proton NMR ($^1$H NMR).

Figure 7:
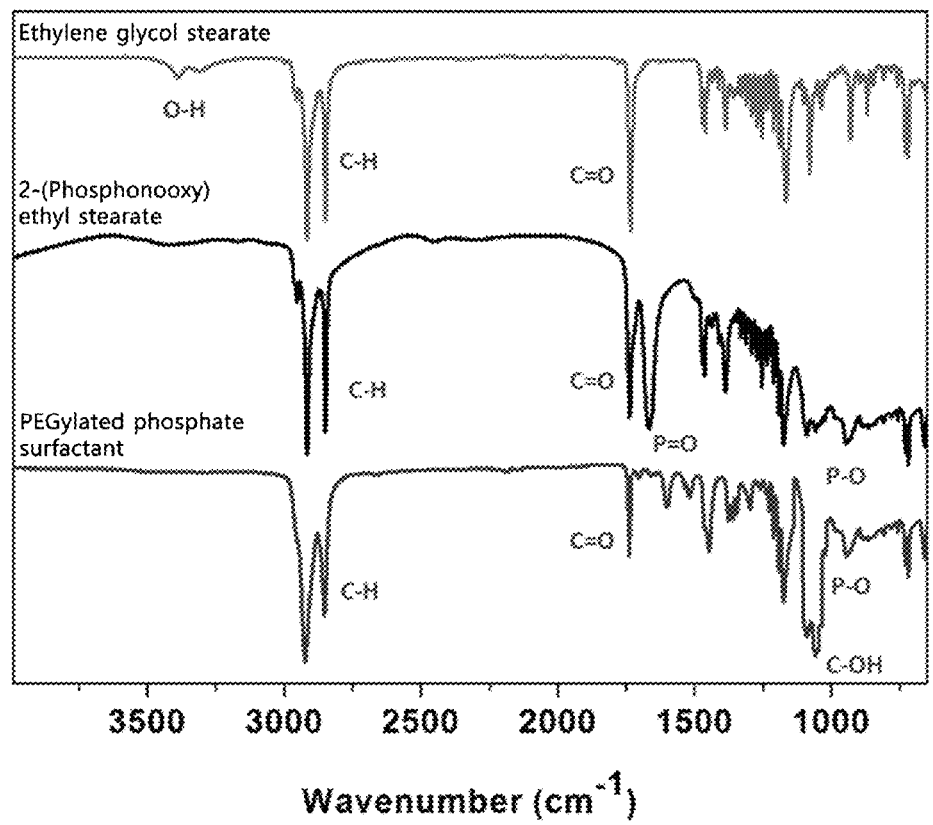
FIG. 7 is FT-IR spectra of ethylene glycol stearate (EGS), 2-(phosphonooxy)ethyl stearate, and a phosphate surfactant finally obtained by PEGylation in order from the top.

Referring to FIG. 7, the FT-IR spectrum shows a peak shift from 1650 $cm^{-1}$ to 1737 $cm^{-1}$, which corresponds to the conversion of the carboxylic acid group to the ester group. Proton NMR (1H NMR) of ethylene glycol stearate confirms the expected structure.

Figure 8:
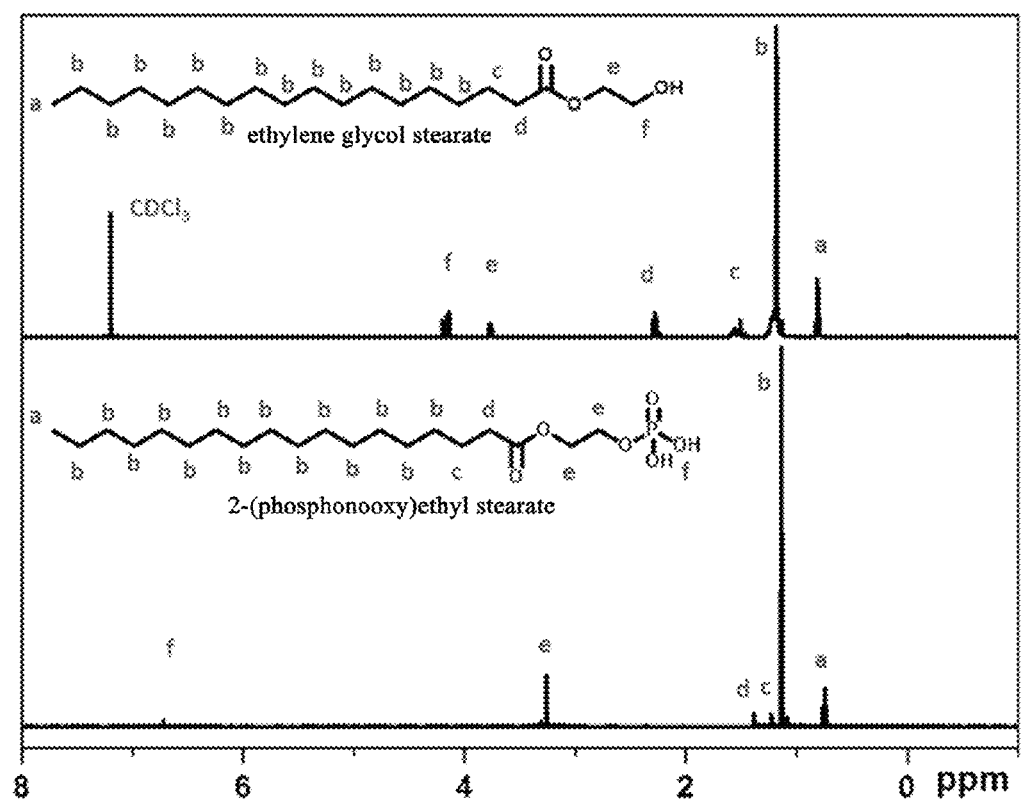
FIG. 8 is $^1$H-NMR spectra of ethylene glycol stearate (EGS) and 2-(phosphonooxy)ethyl stearate in order from the top.

In FIG. 8, the $^1$H NMR of ethylene glycol stearate shows that a broad singlet between 1.26 and 1.31 ppm represents hydrogen from fatty acids and a triplet at 0.88 ppm is associated with the methyl group of stearic acid. The multiplet present at 1.64 ppm is related to the hydrogen on the β carbon, while the hydrogen on the α carbon appears in the triplet at 2.32 ppm. Triplets at 3.65 and 4.20 ppm are related to methylene hydrogen in the ethylene glycol moiety.

Figure 9:
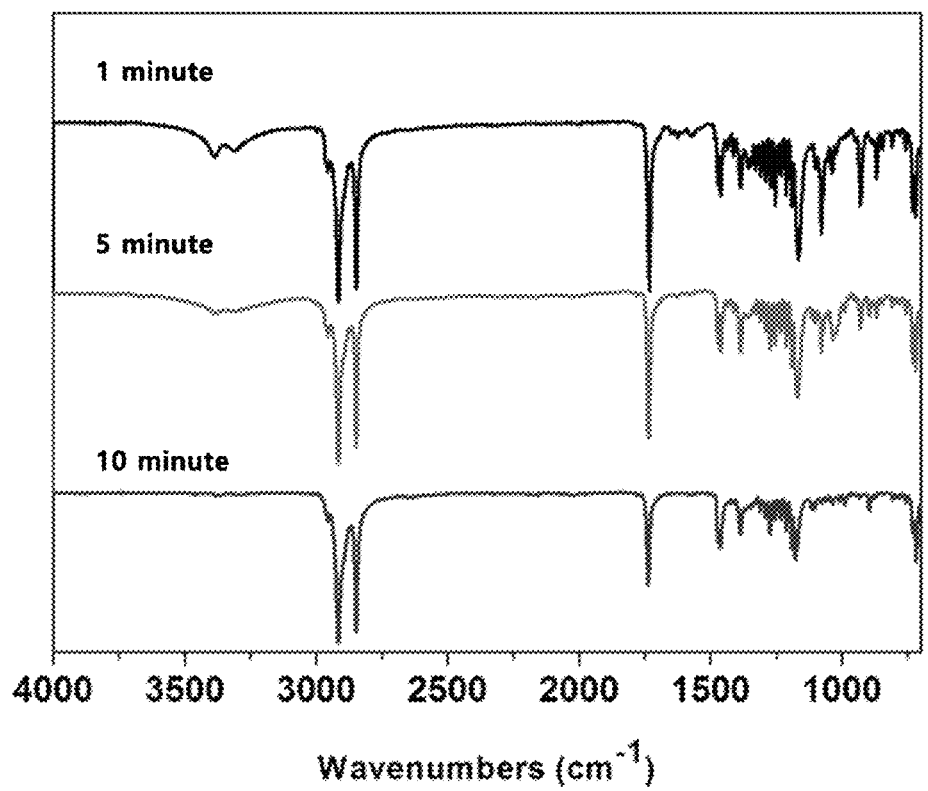
FIG. 9 is an FT-IR spectrum of ethylene glycol stearate when the time for washing with methanol is 1 minute, 5 minutes, or 10 minutes.
Figure 10:
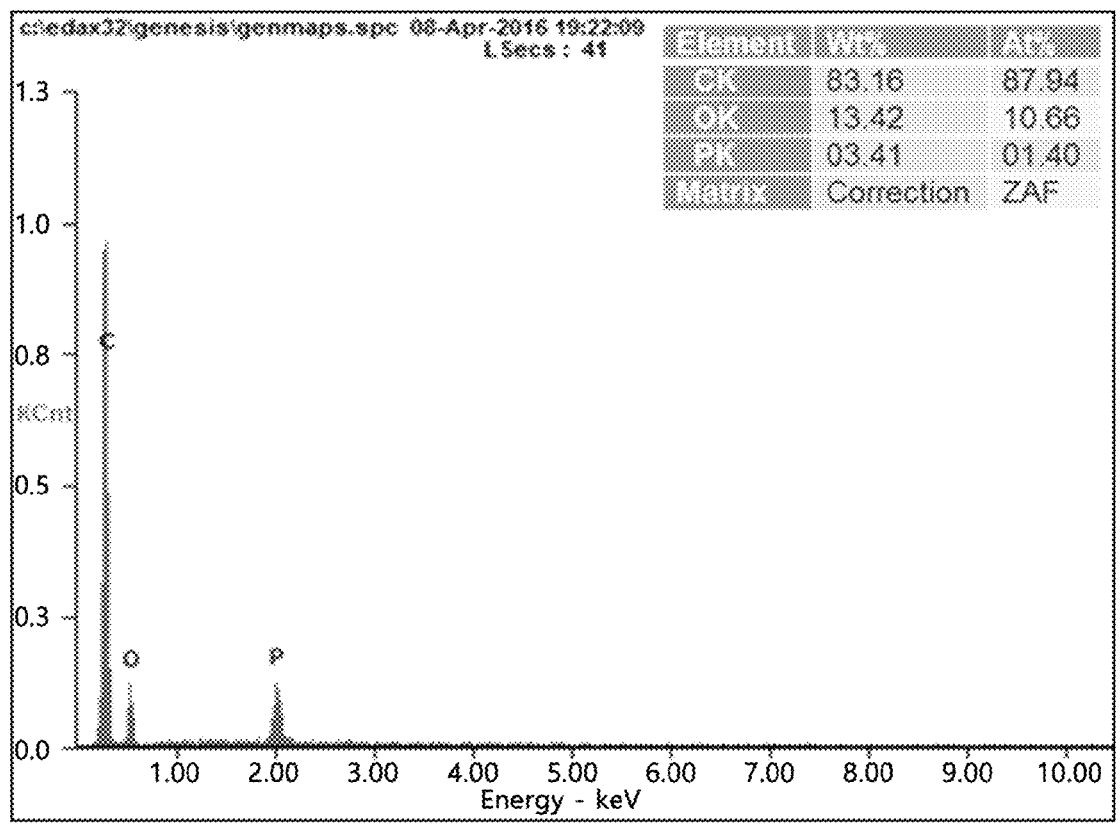
FIG. 10 is the result of EDAX analysis for a surfactant after monophosphorylation of ethylene glycol stearate.

As noted above, dicyclohexylurea (DCU) was still present in the product even after washing with sodium bicarbonate and a diluted hydrochloric acid solution. Thus, the product obtained in a crystal form was washed with methanol. Since DCU has high solubility in methanol, the product was washed several times with methanol. FIG. 9 shows that agitation in methanol for 5 minutes is most appropriate because DCU is not completely removed when agitating for less than 5 minutes. When agitation is performed for 5 minutes or more, on the other hand, the product is damaged. The peak at 3326 $cm^{-1}$ in the FT-IR spectrum is associated with the N—H stretch of DCU overlapping the O—H stretch of EGS.

2) Second Step: Synthesis and Purification of 2-(Phosphonooxy) Ethyl Stearate

Dehydration condensation of phosphoric acid and ethylene glycol stearate promoted by a nucleophilic base (tributylamine) was used for the synthesis of phosphate monoesters. This method is a method for synthesizing phosphoric acid monoesters by directly condensing equimolar phosphoric acid and ethylene glycol stearate. An azeotropic solvent ($DMF/EtNO_2$) was selected because a high reaction temperature is not desirable for green synthesis. 3 mmol (1.18 g) of ethylene glycol stearate (EGS) was dissolved in a solvent and agitated with low heat to completely dissolve EGS. Then, 3 mmol (0.71 ml) of tributylamine ($Bu_3N$) and 10 mol % (0.037 g) of dimethylaminopyridine (DMAP) were added to the reaction medium. Finally, 3.04 mmol (3.46 ml) of phosphoric acid (PA) was added thereto and the resultant mixture was heated to reflux. A Dean-Stark apparatus was used to remove water and consequently control a reaction time. After the reaction medium was cooled to room temperature, recrystallization of a liquid phase was performed. The product was washed with ethyl acetate to remove unreacted 2-(phosphonooxy) ethyl stearate.

Characterization of the product was performed using FT-IR and $^1$H NMR.

The peak appearing at 1737 $cm^{-1}$ in FIG. 7 is associated with the ester group. Another peak appearing between 920 $cm^{-1}$ and 1088 $cm^{-1}$ confirms the presence of a P—O—C bond. Also, the peak positioned between 1600 $cm^{-1}$ and 1700 $cm^{-1}$ indicates the presence of an O=P—OH group.

In FIG. 8, the proton NMR indicates the formation of a phosphate surfactant. A triplet of 0.75 ppm is associated with the methyl group of stearic acid, and a broad singlet between 1.12 and 1.16 ppm represents hydrogen from fatty acids. The peaks were shifted to low ppm because of different solvents.

3) Third Step: Synthesis and Purification of PEGylated 2-(Phosphonooxy)Ethyl Stearate PEGylation of a phosphate group in a 2-(phosphonooxy) ethyl stearate polymer was achieved using Steglich esterification. After 0.1 mol (0.195 g) of 2-(phosphonooxy)ethyl stearate was dissolved in 30 ml of dichloromethane (DCM), 2 equivalents (0.9310 g) of polyethylene glycol (PEG) were added thereto and agitation was performed in an ice-water bath, thus cooling the reaction medium. In order to promote the reaction, 10 mol % of 4-dimethylaminopyridine (DMAP) was used as a catalyst. After the reaction medium was cooled to 0° C., a solution which contained 0.227 g of dicyclohexylcarbodiimide (DCC) in 20 ml of DCM and which was prepared in advance was added dropwise thereto. After all of the DCC was added, the ice-water bath was removed and the reaction medium was agitated at room temperature for two days in the presence of nitrogen. Subsequently, the reaction medium was filtered and the solvent was evaporated using a rotary evaporator. The oily product was washed with ethyl acetate to remove a small amount of catalyst.

According to FIG. 7, it can be confirmed that successful PEGylation was achieved, and the strong peak positioned between 3000 $cm^{-1}$ and 2820 $cm^{-1}$ indicates an increase in the number of aliphatic hydrocarbons. The peak at 1737 $cm^{-1}$ confirms the presence of an ester group between the fatty acid and ethylene glycol. The peak positioned between 1000 $cm^{-1}$ and 1100 $cm^{-1}$ confirms the presence of the P—O—C group and the presence of the polyethylene glycol chain in phosphorus (P). Since the polyethylene glycol chain replaces the hydroxyl group of the phosphate, the peak positioned in the range of 1600 $cm^{-1}$ to 1700 $cm^{-1}$ migrates to a lower wavelength and the intensity thereof is decreased.

Figure 11:
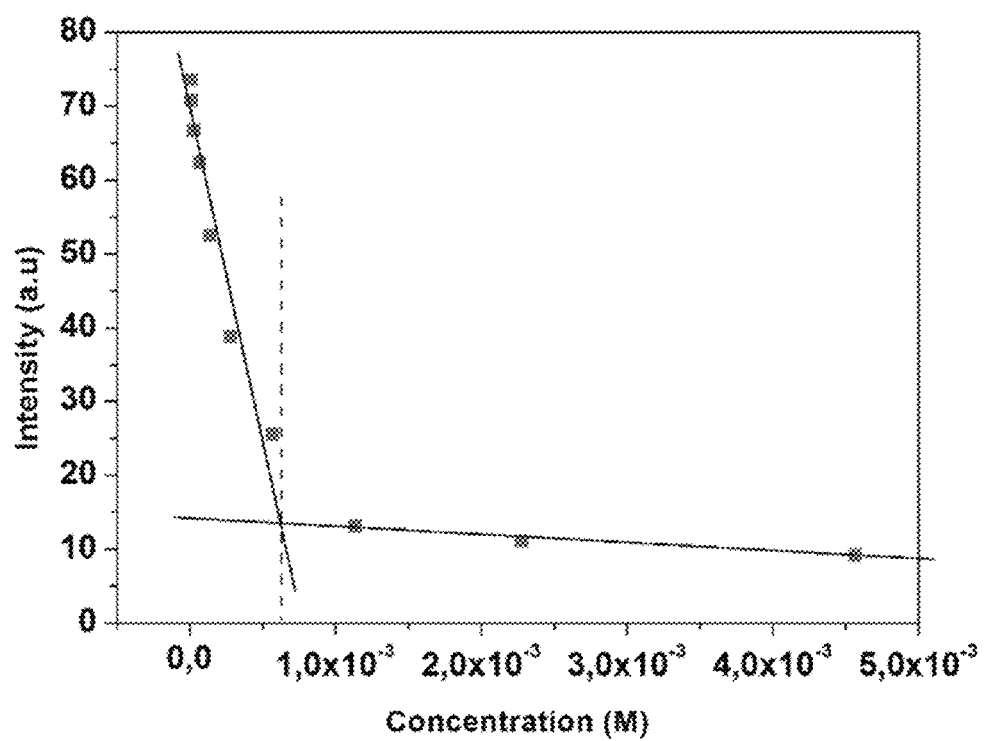
FIG. 11 is a graph showing the change in fluorescence intensity versus the logarithm of the phosphate surfactant concentration in order to determine the critical micelle concentration (CMC) of a phosphate surfactant.

Further, a critical micelle concentration (CMC), indicating the main properties of the surfactant, was measured through a dye micellization method using Rhodamine B. After the Rhodamine B solution was mixed with a phosphate polymer solution, the photoluminescence of each solution was measured. The sample was excited at 510 nm. The dye micellization method is based on the change in the fluorescence intensity of the dye after addition of the surfactant. As the concentration of the surfactant increases, the strength decreases. FIG. 11 shows that micelles were formed at a concentration of $6.38 \times 10^{-4}$ M. From comparison with conventional documents, it can be seen that the CMC of the new monomer surfactant is relatively similar to that of the other monomer surfactant.

Next, digestion and liquid chromatography tandem mass spectrometry (LC/MS) were performed in order to confirm the activity of bee venom sPLA-2 on the phosphate surfactant. The activated bee venom sPLA-2 was used for digestion of the polymer, and then the cut fragments were confirmed using a liquid-chromatography-coupled mass spectrometer (LC/MS). As a substrate, a second-stage polymer having a molecular weight lower than that of the PEGylated polymer was used.

Figure 12:
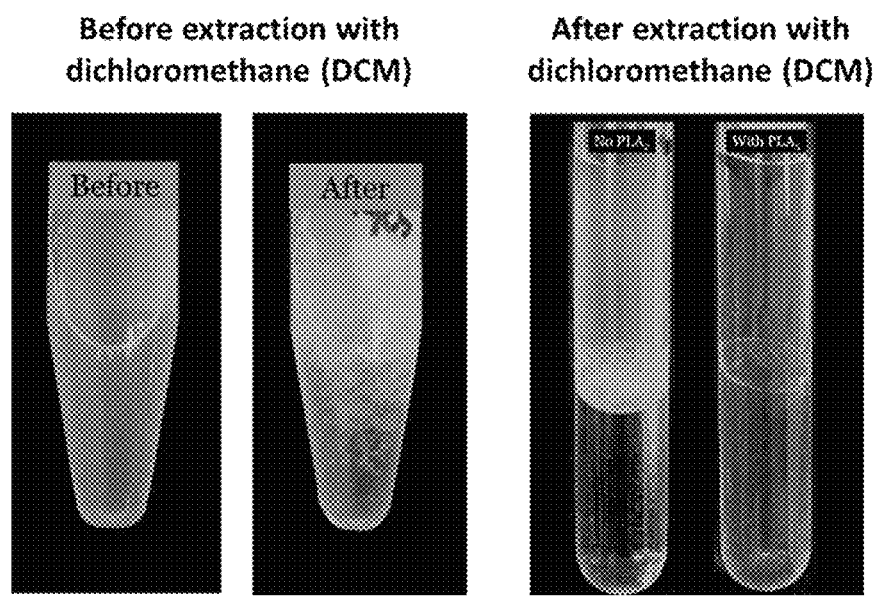
FIG. 12 is a photograph showing physical changes after digestion when sPLA-2 is added to the phosphate surfactant.

According to FIG. 12, a physical change in the solution was observed after addition of the enzyme to the phosphate surfactant. Specifically, after adding the sPLA-2 enzyme to the solution containing the phosphate surfactant, the formation of an insoluble material was observed in the water moving to the top of the tube, and it is assumed that this is because stearic acid, which is insoluble in water and which has a density relatively lower than that of water, moves to the upper portion of the tube after the phosphate surfactant is digested. Further, it was observed that the aqueous phase of the treated sample was much cleaner and more transparent during the extraction of the sample in dichloromethane (DCM) prior to injection into the LC/MS. Steric acid released after the cleavage of phosphate surfactant by sPLA-2 is readily soluble in DCM.

Figure 13:
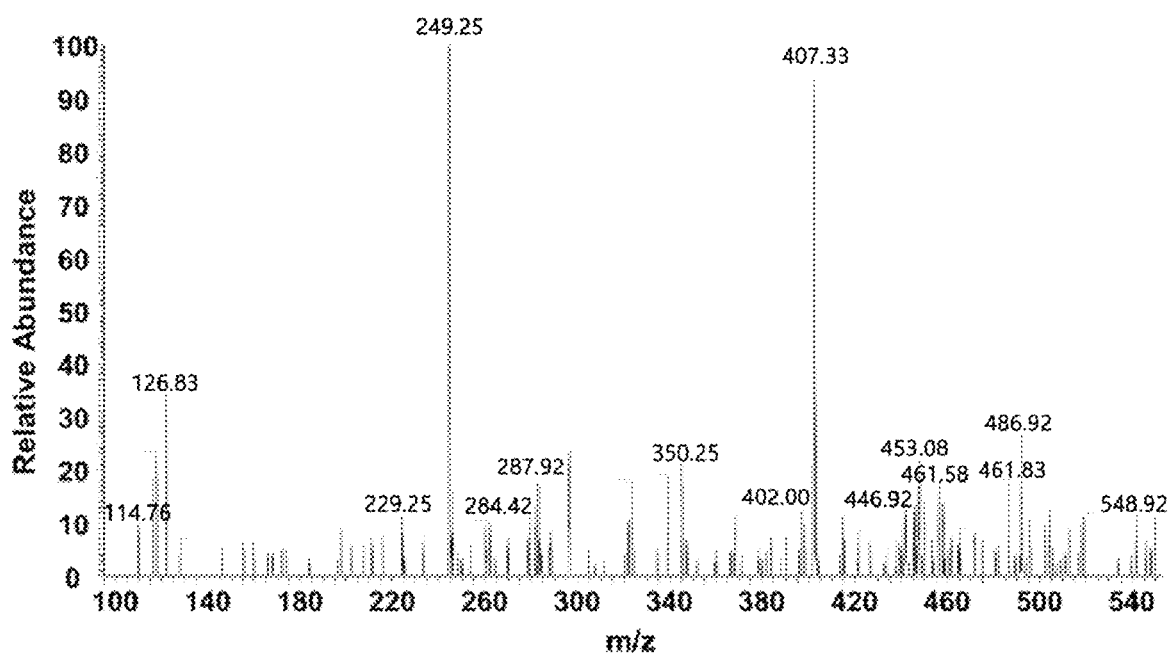
FIG. 13 is a mass spectrum of the phosphate surfactant before digestion with an sPLA-2 enzyme.
Figure 14:
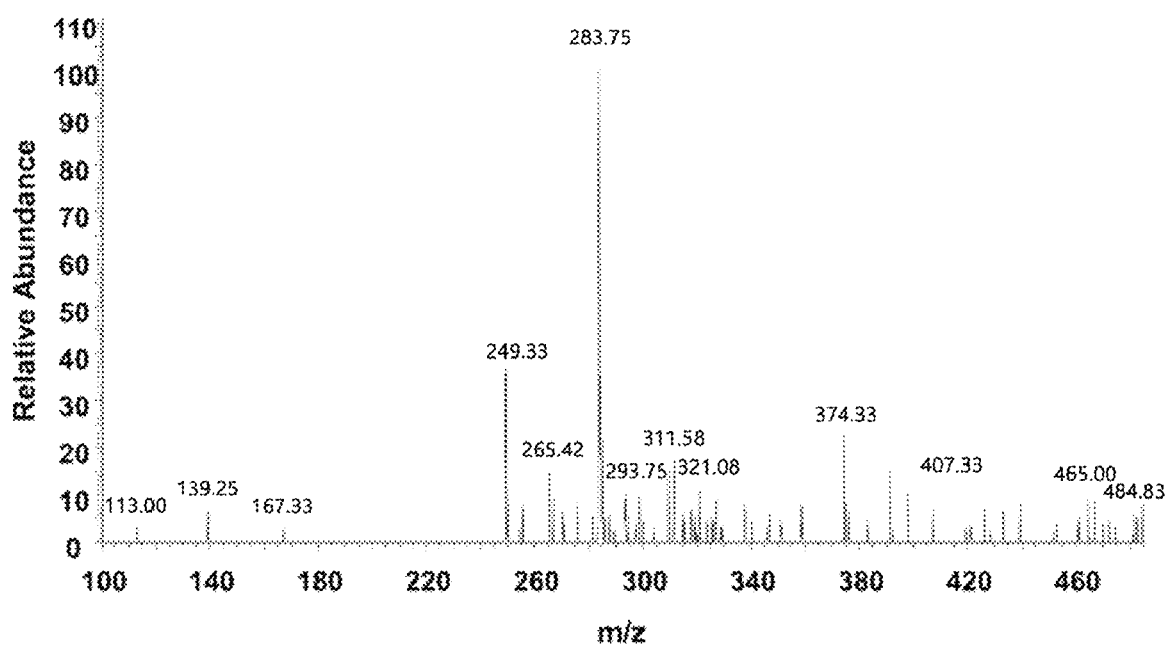
FIG. 14 is a mass spectrum of the phosphate surfactant after digestion with an sPLA-2 enzyme.

Referring to FIGS. 13 and 14, the mass spectrum of the solution containing only the polymer has a peak at 407.90 m/z, corresponding to the phosphate surfactant. The intensity of the peak at 407.90 m/z is very low compared to the noise peak. This means that since a large amount of phosphate surfactant remains in an aqueous phase due to the solubility of the phosphate surfactant in water during extraction with dichloromethane (DCM), the concentration of the phosphate surfactant is very low. On the other hand, the post-injection mass spectrum shows that the peak at 407.90 m/z disappears, indicating that the phosphate surfactant is hydrolyzed by the enzyme to thus form stearic acid appearing at 284 m/z.

(3) Encapsulation of UCNP in Micelle

In order to encapsulate UCNP in micelles, the UCNP was simply sonicated with a phosphate surfactant at room temperature for 30 minutes, thus achieving the encapsulation. Thereafter, the properties of the micelles loaded with the UCNP were analyzed using FT-IR, EDAX, and TEM.

Figure 15:
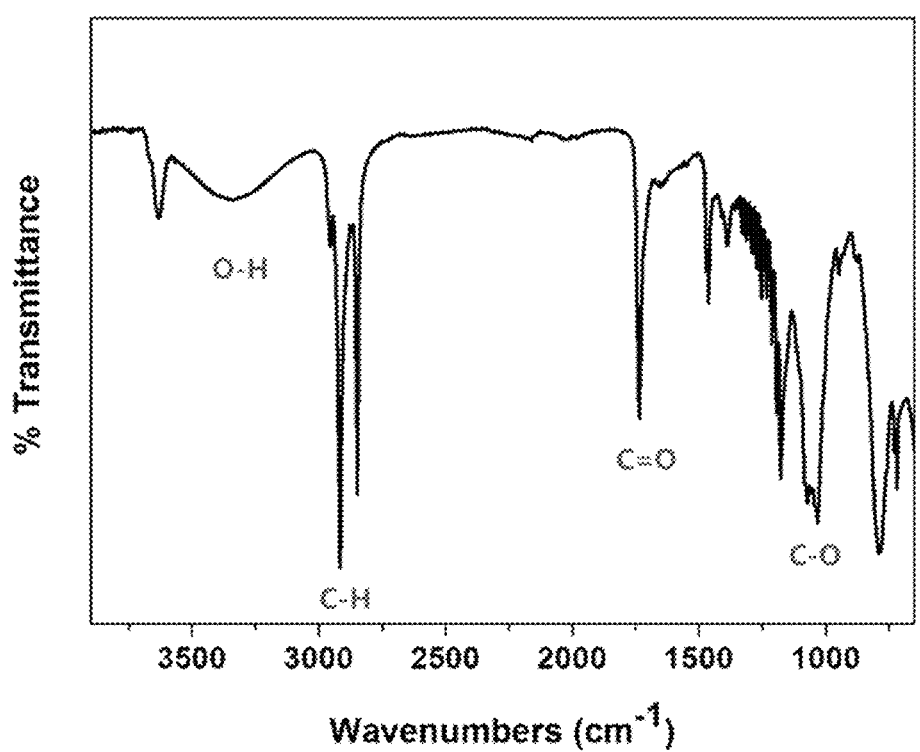
FIG. 15 is an FT-IR spectrum of micelles loaded with NaLuF$_4$:Gd$^3$/YB$^3$/Er$^{3+}$ upconversion nanoparticles.
Figure 16:
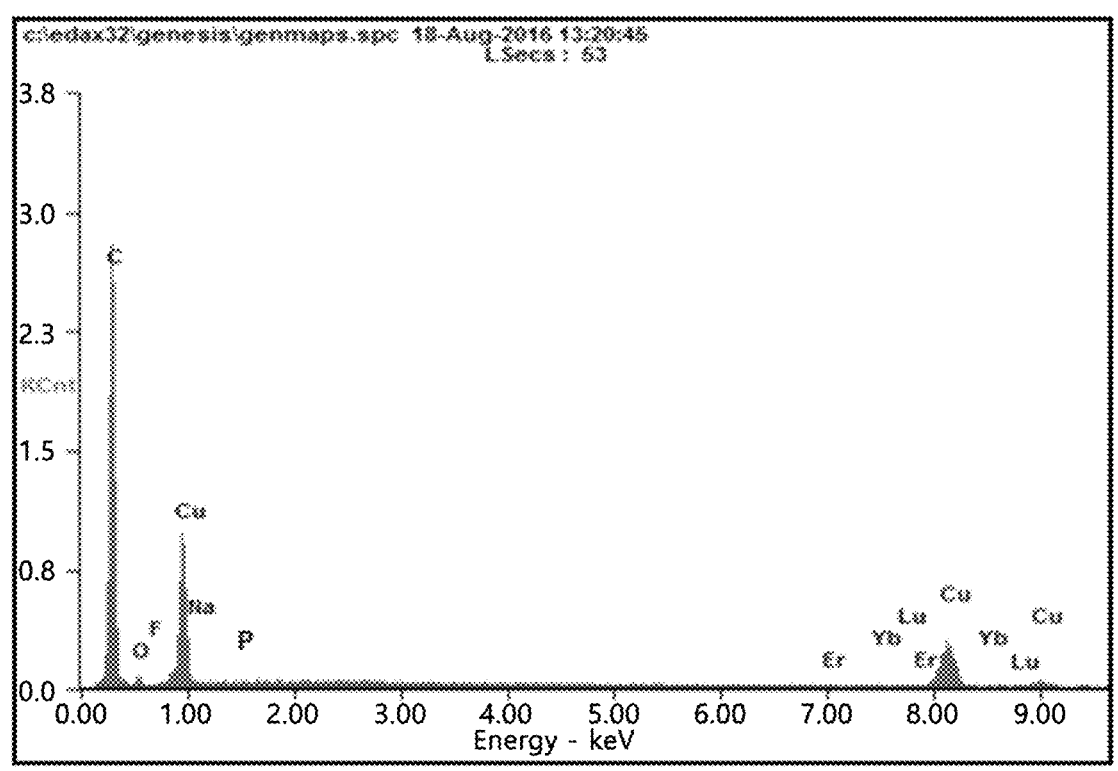
FIG. 16 is the result of EDAX analysis of micelles loaded with the NaLuF$_4$:Gd$^3$/YB$^3$/Er$^{3+}$ upconversion nanoparticles.
Figure 17:
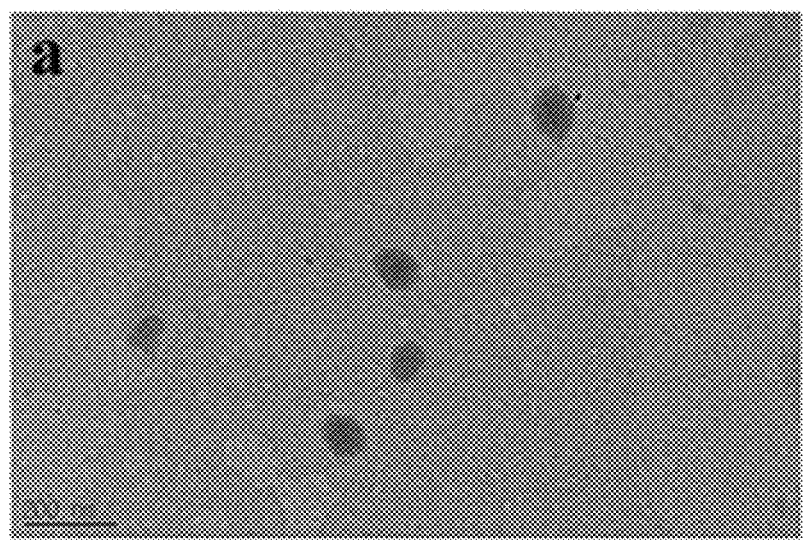
FIG. 17 is a transmission electron microscope (TEM) image of micelles before loading of the upconversion nanoparticles.
Figure 18:
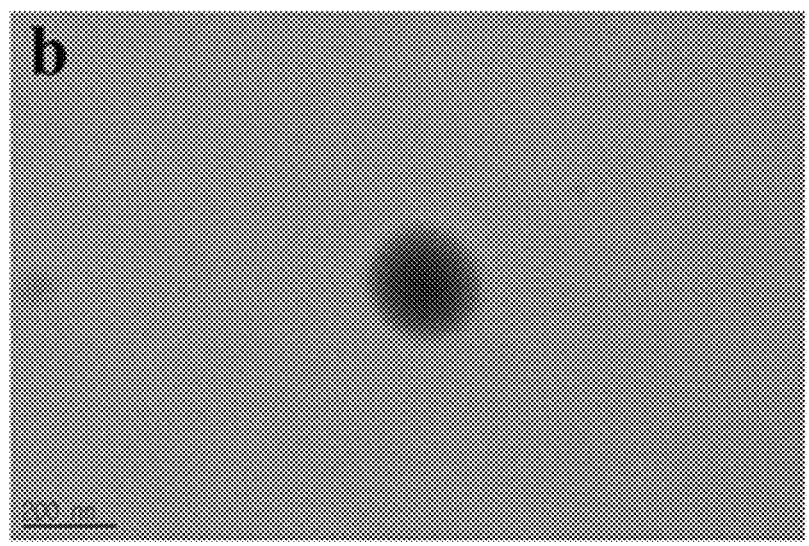
FIG. 18 is a transmission electron microscope (TEM) image of a single micelle before loading of the upconversion nanoparticles.
Figure 19:
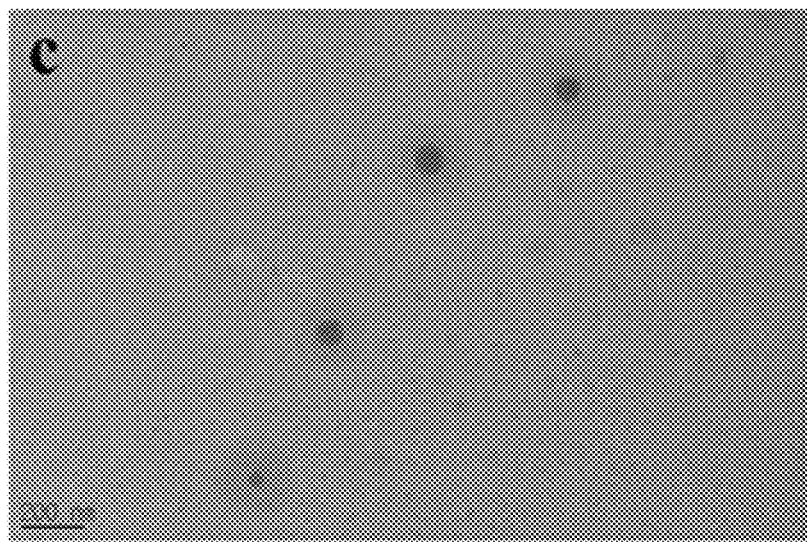
FIG. 19 is a transmission electron microscope (TEM) image of micelles loaded with the upconversion nanoparticles.
Figure 20:
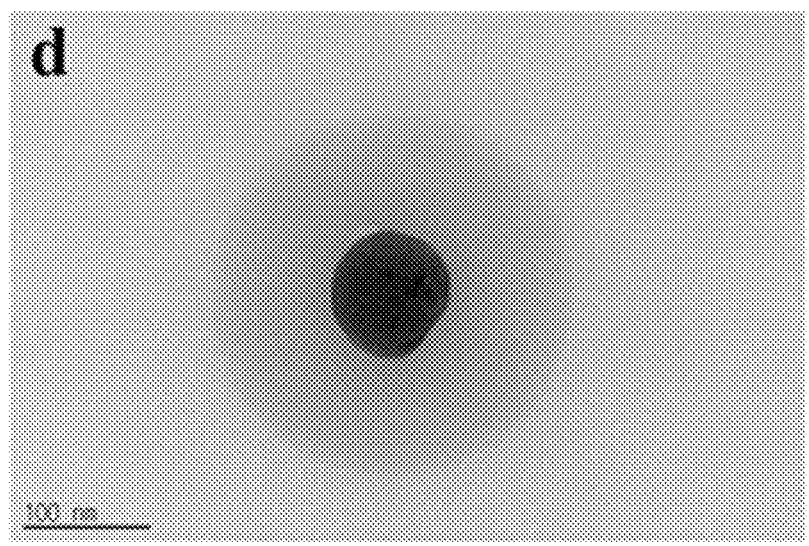
FIG. 20 is a transmission electron microscope (TEM) image of a single micelle loaded with the upconversion nanoparticles.

Since the phosphate surfactant is readily soluble in water due to the presence of PEG chains, the UCNP is dispersed very rapidly with the surfactant. FT-IR was used in order to confirm whether the UCNP was successfully loaded into the micelles (FIG. 15). The corresponding FT-IR spectrum confirms the presence of functional groups of the UCNP and the phosphate surfactant. The broad absorption band around about 3435 $cm^{-1}$ corresponds to the O—H stretching vibration from the UCNP, and the peak at 1737 $cm^{-1}$ is related to the ester group of the phosphate surfactant. As a result of the elemental analysis (EDAX) (FIG. 16), peaks for all of the atoms were observed, as expected. Since the percentage of phosphorus (P) is very small compared to the long hydrocarbon chains of PEG and the surfactant, the peak for the phosphorus (P) atom is relatively low. Since the surfactant was deposited on a copper tape, copper (Cu) ions also appeared in the EDAX spectrum.

Further, the TEM images shown in FIGS. 17 to 20 show that the surface of the particles is mesoporous, thereby confirming that the UCNP is loaded in the micelles. The TEM images confirm that the micelles are between 50 nm and 200 nm in size while the micelles loaded with the UCNP are in the range of 60 nm and 100 nm.

Figure 21:
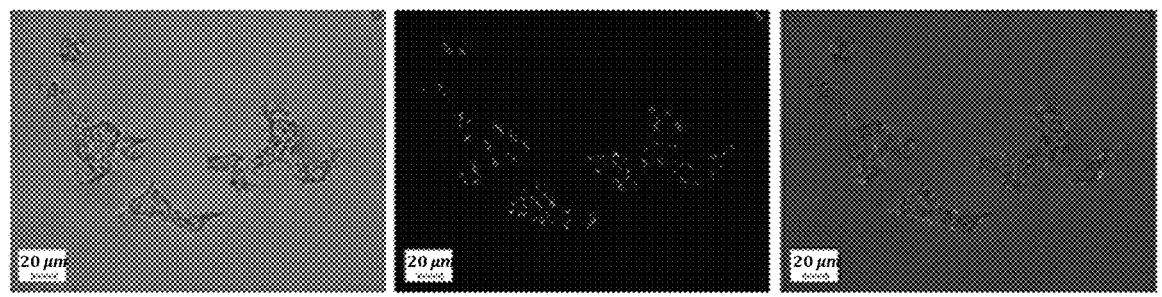
FIG. 21 is a fluorescence image of 22Rv1 cells treated with micelles loaded with the upconversion nanoparticles.
Figure 22:
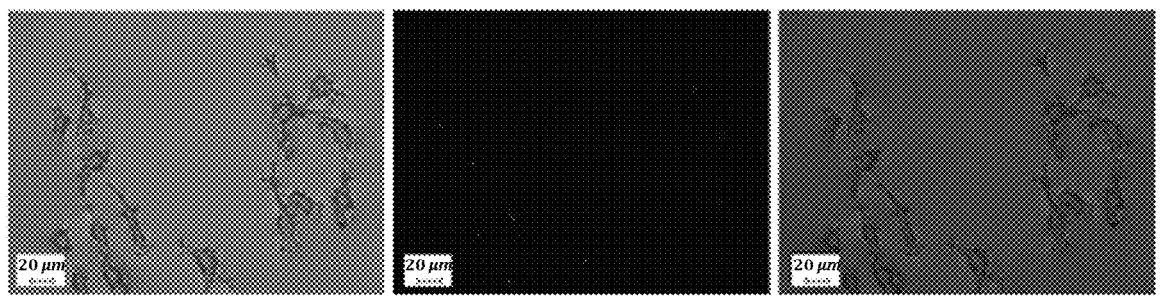
FIG. 22 is a fluorescence image of HeLa cells treated with micelles loaded with the upconversion nanoparticles.
Figure 23:
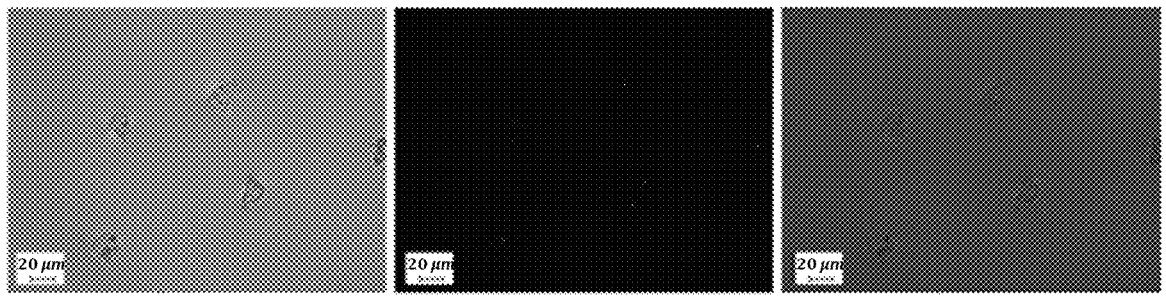
FIG. 23 is a fluorescence image of KB cells treated with micelles loaded with the upconversion nanoparticles.

(4) Cell Imaging Using Phosphate Micelle Particles Loaded with the Manufactured UCNP Three different cells were selected in order to confirm the selectivity of micelles loaded with the UCNP to a prostate cancer cell expressing sPLA-2. HeLa (human cervical cancer, adenocarcinoma) is the most common, resistant, and viable cell line. Further, a KB cell line (HeLa contaminant, carcinoma), which is a relatively fragile, sensitive, and less viable cell, was selected. Neither of the above two cell lines overexpress a sPLA-2 enzyme. On the other hand, a 22Rv1 (prostate carcinoma) cell line is known to overexpress the sPLA-2 enzyme. The experimental result showed the selectivity of the nanoparticles to the 22Rv1 cell line among three different cell lines. From the result of in-vitro bio-imaging analysis, it was confirmed that the encapsulated UCNPs had significantly reduced toxicity to all cells, particularly the sPLA-2 non-expressing cell line. Since the release of the UCNP is directly related to sPLA-2, which is not overexpressed in HeLa and KB cells, the micelles loaded with the UCNP do not have affinity for these types of cells due to the protective shell from the surfactant. FIGS. 22 and 23 show that very weak upconversion fluorescence appears in these two cells. However, since the 22Rv1 cell line overexpresses the sPLA-2 enzyme capable of decomposing the surfactant, the 22Rv1 cell line liberates the UCNP from the surface of prostate cancer cells, and the image of prostate cancer cells is clearly visible through intense upconversion fluorescence (FIG. 21).

Figure 24:
FIG. 24 is a fluorescence image of HeLa cells treated with the upconversion nanoparticles that are not encapsulated in surfactant micelles.
Figure 25:
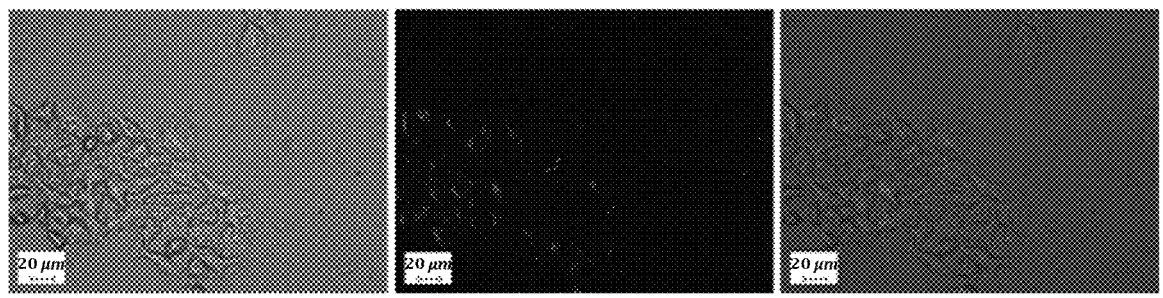
FIG. 25 is a fluorescence image of KB cells treated with the upconversion nanoparticles that are not encapsulated in surfactant micelles.

However, the unencapsulated UCNP exhibits affinity to all cells. FIGS. 24 and 25 show in-vitro bio-imaging results for HeLa and KB cell lines performed using the UCNP not encapsulated in the micelles, in which both cells are surrounded by the UCNP and exhibit intense upconversion fluorescence imaging. However, relative loss of confluency was observed only in the cells treated with the UCNP. That is, the UCNP was relatively less toxic than micelles.

(5) Cytotoxicity Assay of Phosphate Micelle Particles Loaded with the Manufactured UCNP and Unencapsulated UCNP Cytotoxicity is an important factor to be considered in all new nanomaterials, particularly nanomaterials applied to nanomedicine.

Figure 26:
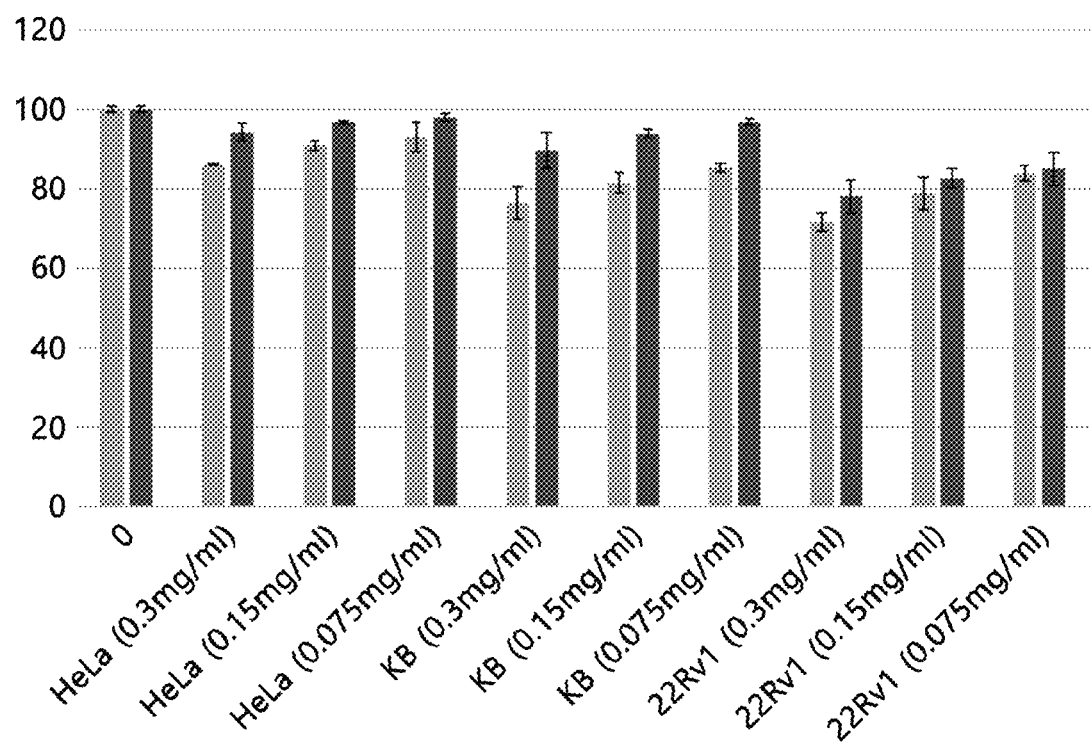
FIG. 26 shows the results of cytotoxicity assay (MTT assay) of micelles loaded with upconversion nanoparticles on 22Rv1 cells, HeLa cells, and KB cells.

Referring to the following table and FIG. 26, the result of MTT analysis shows that the encapsulated UCNP exhibited decreased toxicity for three different cells. At concentrations of 300 µg/mL of the UCNP and 0.002M phosphate surfactant, the cytotoxicity was reduced to 7.98%, 13.16%, and 6.47% for the HeLa, KB, and 22Rv1 cell lines, respectively. However, the cytotoxicity for the 22Rv1 cell line is still high, which can be explained by the cleavage of the phosphate surfactant and the liberation of the UCNP at high concentration on the cell surface.

|  | HeLa | KB | 22Rv1 |
|---|---|---|---|
| Treated with UCNP | 86.23% | 76.49% | 71.60% |
| Treated with micelle loaded with UCNP | 94.21% | 89.65% | 78.07% |

<Example 2> Manufacture of Phosphate Micelle Particles Loaded with Therapeutic Agent for Prostate Cancer (Estramustine Phosphate)

(1) Entrapment of Drug into Micelle Including Phosphate Surfactant

The entrapment of estramustine phosphate into micelles including the phosphate surfactant manufactured in 'Example 1' was performed in a PBS solution.

For reference, the estramustine phosphate is a double alkylated antineoplastic agent (i.e., chemotherapeutic drug) and an estrogen-type hormone antineoplastic agent, respectively sold under the trade names Emcyt and Estracyt and used for prostate cancer therapy.

Specifically, after 0.022 g of the phosphate surfactant was dispersed in 4 ml of PBS, estramustine phosphate sodium (1400 µg) was added to the phosphate surfactant solution. The resultant solution was agitated at 37° C. for 24 hours. Thereafter, the product was collected by centrifugation at 4000 rpm for 20 minutes and subjected to decantation and redispersion three times in the PBS solution. Dialysis (MW cutoff 3500) was performed in order to remove the estramustine phosphate that was not loaded.

In addition, the supernatant and the washing solution were collected to further quantify the entrapped estramustine phosphate using UV absorption spectroscopy at 215 nm.

Figure 27:
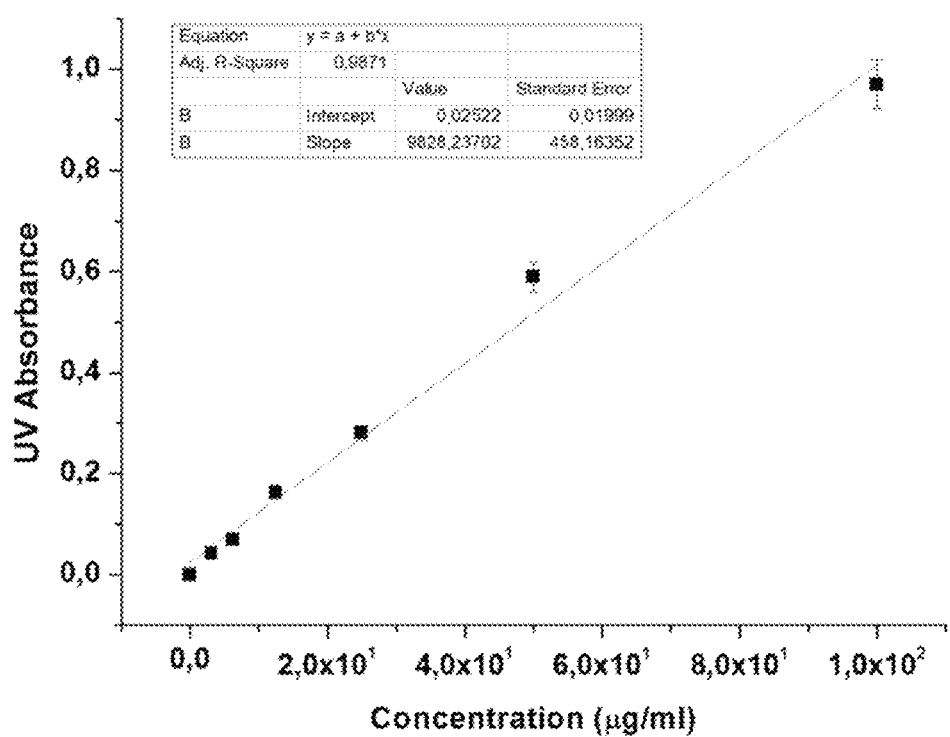
FIG. 27 is a calibration curve of estramustine phosphate sodium in a PBS solution.

A calibration curve was prepared in consideration of the importance of the entrapment and release efficiency calculation. For this purpose, a series of solutions having different concentrations of estramustine phosphate was prepared, the estramustine phosphate sodium (0.001 g) was dissolved in 10 mL of the PBS (phosphate buffered saline×1) solution, and a ½ dilution process was repeated 5 times. In addition, the UV absorption spectrum of the solution was collected, and a calibration curve thereof was prepared (FIG. 27).

Figure 28:
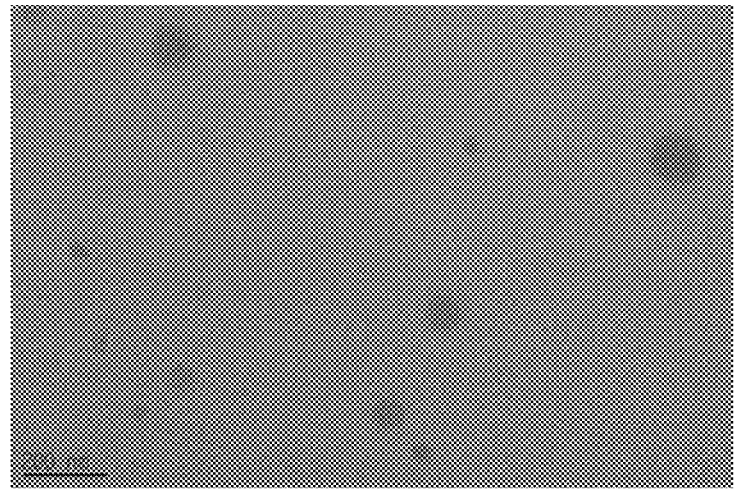
FIG. 28 is a transmission electron microscope (TEM) image of micelles before the entrapment of estramustine phosphate.
Figure 29:
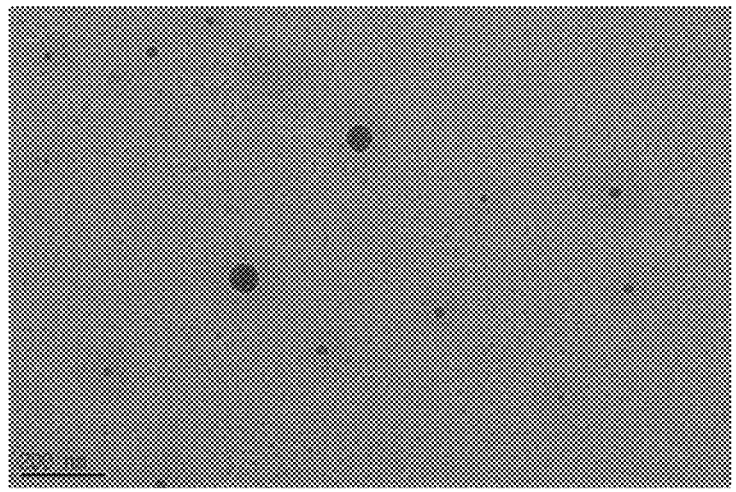
FIG. 29 is a transmission electron microscope (TEM) image of micelles after the entrapment of estramustine phosphate.

The entrapment efficiency (EE %) was calculated using the calibration curve and the following Equation. As a result, the entrapment efficiency was found to be 81,432% of the initial concentration. Further, the TEM images of the micelles before and after the drug entrapment showed that the estramustine phosphate was successfully entrapped in the micelles (FIGS. 28 and 29).

$$EE\ \% = \frac{\text{Total}_{Drug} - \text{Free}_{Drug}}{\text{Total}_{Drug}} \times 100$$

(2) Measurement and Analysis of Release Efficiency of Estramustine Phosphate onto Micelle Entrapping the Manufactured Estramustine Another important property of the drug delivery system is the release efficiency of the entrapped drug through triggering. Since the phosphate surfactant according to the present invention may be cleaved by sPLA-2, the drug release experiment was performed using sPLA-2, which is extracted from an activated bee venom material, as a triggering agent.

Specifically, in order to stimulate drug releasing, the micelles loaded with the estramustine phosphate manufactured in the above Example were dispersed in a 4 ml PBS solution containing 6 to 24 U/L of activated bee venom sPLA-2 and 2 mM $CaCl_2$). The solution was agitated at 37° C. for minutes and then subjected to centrifugation to thus separate the solution containing the drug released from pellets containing the s-PLA and micelles. Thereafter, the micelles were redispersed in a solution of sPLA-2 and further agitated for 20, 60, and 180 minutes.

Figure 30:
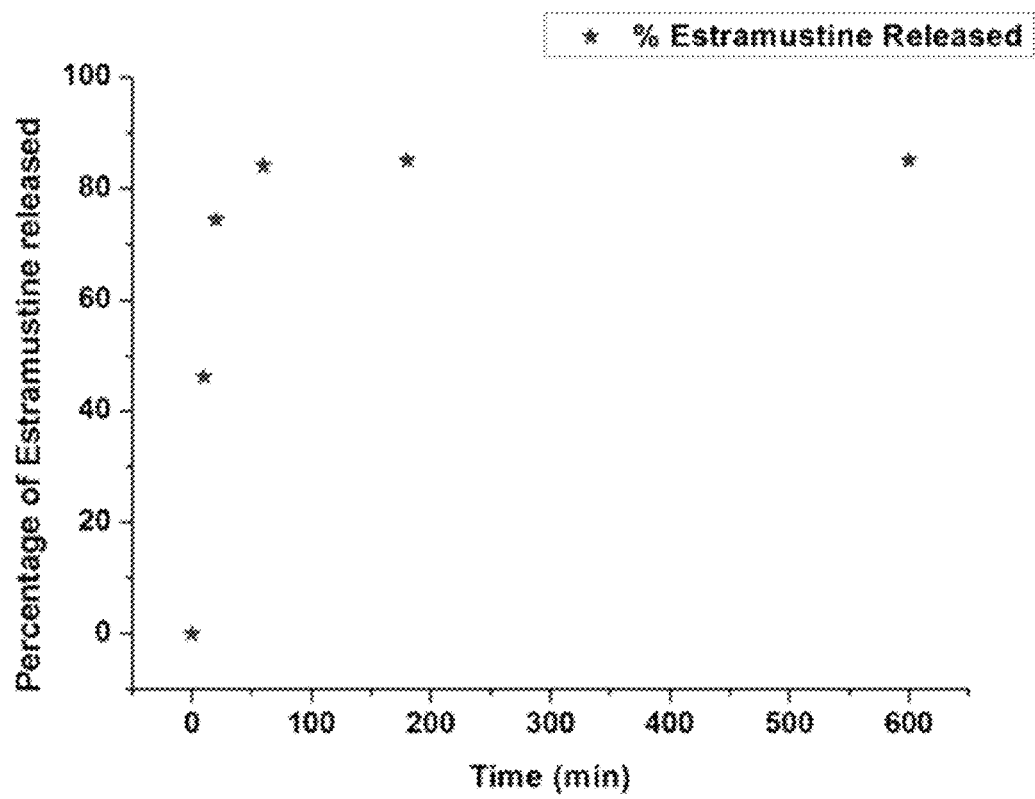
FIG. 30 is the measurement result of the release efficiency of estramustine induced by phosphate surfactant cleavage due to activated bee venom sPLA-2.

The cumulative release amount of estramustine from the micelles loaded with the estramustine phosphate in the presence of sPLA-2 is shown in FIG. 30. The cumulative amount of the released estramustine salt reached 85.12% after incubation at a pH of 7.4 and 37° C. for 24 hours. Interestingly, 84.12% of the drug was released after the elapse of the first 1 hour, which means that almost all of the estramustine phosphate loaded for about 1 hour after the start of release was released from the micelles.

(3) Cytotoxicity Assay of Micelle Particles Entrapping the Manufactured Estramustine and Estramustine Cytotoxicity is an important factor to be considered in all new nanomaterials, particularly nanomaterials applied to nanomedicine.

In the present Experimental Example, the cell viability of cancer cells for the KB cell line (HeLa contaminant, carcinoma) and the 22Rv1 (human prostate cancer, carcinoma) cell line was confirmed using an MTT assay (3-[4,5-dimethylthiazol-2-yl]-2,5-diphenyltetrazolium bromide).

For this, cells were grown in MEM (Minimum Eagle's medium) and RPMI 1640 medium (ATCC modification). All media were supplemented with 10% FBS (fetal bovine serum) and 5 mL of Pen/Strep (10.000 µg/mL, 10.000 units/mL) at 37° C. under 5% $CO_2$. The 22Rv1 and KB cells were inoculated into a 96-well cell incubation plate at $10^4$/L/well, followed by adhesion at 37° C. for 24 hours under 5% $CO_2$.

Next, the micelles in which the estramustine phosphate manufactured in the Example was entrapped were dispersed in the RPMI 1640 (ATCC modification) and MEM media. Separately, only the estramustine phosphate not entrapped in the micelles was dispersed in each of the RPMI 1640 (ATCC modification) and MEM media. The media in 96-wells were suctioned and fresh media were added to set negative control, while prepared solutions were added to the treatment group.

In addition, the cells were incubated at 37° C. under 5% $CO_2$ for 24 hours. Subsequently, 100 μL MTT (5 mg/mL) was added to each of wells of the treatment group and the negative control group of a 96-well assay plate, followed by additional incubation for 4 hours at 37° C. under 5% $CO_2$. After 100 μL/well of a DMSO-ethanol solution (1:1) was added, the assay plate was maintained at room temperature for 15 minutes. OD 570 (Abs value) of each well was measured through background subtraction at 540 nm using a Tecan Infinite M200 monochromator-based multi-functional microplate reader.

Figure 31:
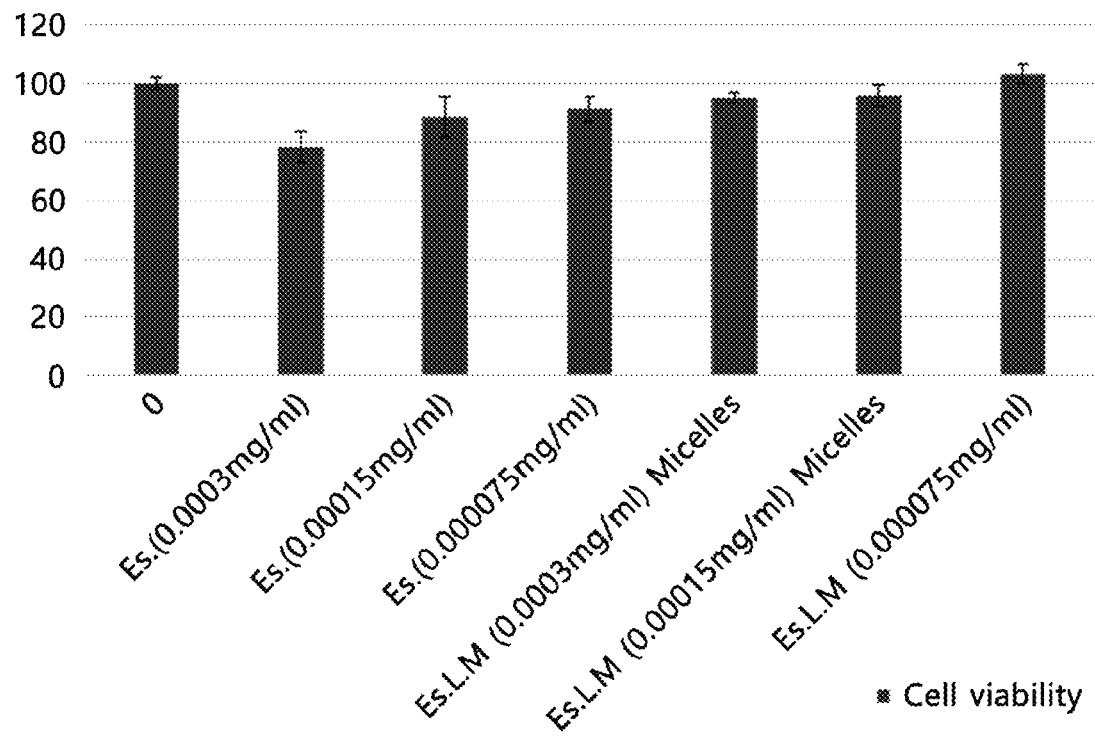
FIG. 31 shows the results of a cytotoxicity assay (MTT assay) of estramustine or estramustine entrapped in micelles for KB cell lines.
Figure 32:
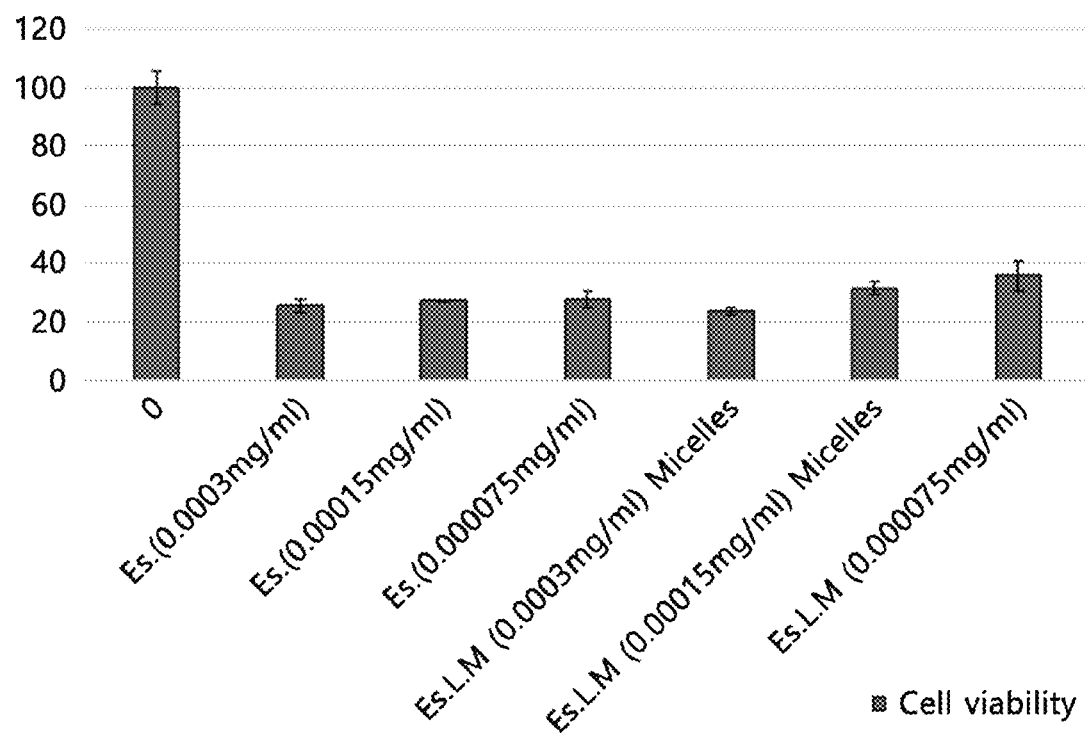
FIG. 32 shows the results of a cytotoxicity assay (MTT assay) of estramustine or estramustine entrapped in micelles for 22Rv1 cell lines.

FIGS. 31 and 32 show the results of cytotoxicity assay (MTT assay) of estramustine or estramustine entrapped in the micelles for the KB cell line and the 22Rv1 cell line, respectively.

Referring to FIGS. 31 and 32, it can be confirmed that the cell viability of the KB cell line treated with estramustine entrapped in the micelles was increased compared to estramustine not entrapped in the micelles.

In the case of 0.3 μg/mL of estramustine not entrapped in the micelles, it needs to be noted that the 22Rv1 cell line exhibited cell viability of 25.58% and the KB cell line exhibited cell viability of 78.50%, so the toxicity to the KB cell line was lower.

However, the cell viability of the KB cell line treated with the micelles loaded with the estramustine phosphate was increased to 95.1%, which confirms the entrapment of estramustine by the micelles.

On the other hand, the 22Rv1 cell line treated with the micelles loaded with the estramustine phosphate did not exhibit any change in cell viability.

In conclusion, the above results confirm that the 22Rv1 cell line overexpressing the sPLA-2 enzyme induces cleavage of the micelles and also induces the additional release of estramustine phosphate from the micelles.

INDUSTRIAL APPLICABILITY

The nanocarrier according to the present invention is capable of selectively releasing therapeutic agent and/or diagnostic agent particles on the surface of a prostate cancer cell and has improved dispersibility in the living body. Accordingly, the nanocarrier is useful as an active ingredient of a drug delivery substance and an imaging agent composition for therapy and/or diagnosis of prostate cancer.

The invention claimed is:

1. A nanocarrier for targeted therapy and/or diagnosis of a prostate cancer cell, the nanocarrier comprising:
    a micelle including a phosphate surfactant represented by a following Chemical Formula,
    wherein an ester group contained in a phosphate surfactant is hydrolyzed by a secretory phospholipase A2 (sPLA-2) overexpressed in the prostate cancer cell, thus releasing the therapeutic agent, diagnostic agent particles, or both the therapeutic agent and the diagnostic agent particles:

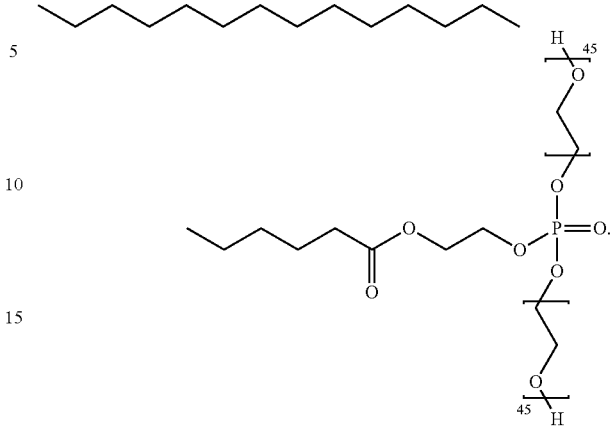

[Chemical Formula]

2. Bio-imaging particles comprising:
    the nanocarrier of claim 1; and
    a diagnostic agent loaded on the nanocarrier.
3. The bio-imaging particles of claim 2, wherein the diagnostic agent is a fluorescent agent, a radioactive agent, or a contrast medium.
4. The bio-imaging particles of claim 2, wherein the diagnostic agent is upconversion fluorescent nanoparticles.
5. The bio-imaging particles of claim 4, wherein the upconversion fluorescent nanoparticles include NaAF4:B1/B2/B3 (A is a lanthanide element and B1, B2, and B3 are different rare earth elements).
6. The bio-imaging particles of claim 5, wherein A is one selected from the group consisting of Y, Tb, Dy, Ho, Tm, Lu, La, Ce, Pr, Nd, Pm, Sm, and Eu.
7. The bio-imaging particles of claim 5, wherein B1, B2, and B3 are different from each other and are each one selected from the group consisting of Yb, Er, Sc, Y, La, Ce, Pr, Nd, Pm, Sm, Eu, Gd, Tb, Dy, Ho, Tm, and Lu.
8. A diagnosis method of prostate cancer, the diagnosis method comprising:
    disposing the bio-imaging particles of claim 2 in a biological environment; and
    selectively releasing diagnostic agent particles onto a surface of a prostate cancer cell positioned in the biological environment, thus performing delivery.
9. A drug delivery substance comprising:
    the nanocarrier of claim 1; and
    a prostate cancer therapeutic agent loaded on the nanocarrier.
10. A prostate cancer therapy method, the therapy method comprising:
    disposing the drug delivery substance of claim 9 in a biological environment; and
    selectively releasing therapeutic agent particles onto a surface of a prostate cancer cell positioned in the biological environment, thus performing delivery.
11. A pharmaceutical composition for prostate cancer therapy comprising:
    the drug delivery substance of claim 9 as an active ingredient.
12. The pharmaceutical composition for prostate cancer therapy of claim 11, wherein the pharmaceutical composition is in a form of an injection, a liquid medicine, a powder remedy, a suspension, a granule, a syrup, a capsule, a pill, or a tablet.

* * * * *